US007989459B2

(12) United States Patent
Roughton et al.

(10) Patent No.: US 7,989,459 B2
(45) Date of Patent: *Aug. 2, 2011

(54) PURINONES AND 1H-IMIDAZOPYRIDINONES AS PKC-THETA INHIBITORS

(75) Inventors: Andrew Roughton, Plainsboro, NJ (US); Yajing Rong, Monmouth Junction, NJ (US); Koc Kan Ho, West Windsor, NJ (US); Michael Ohlmeyer, Plainsboro, NJ (US); David Diller, East Windsor, NJ (US)

(73) Assignee: Pharmacopeia, LLC, San Diego, CA (US)

( * ) Notice: Subject to any disclaimer, the term of this patent is extended or adjusted under 35 U.S.C. 154(b) by 655 days.

This patent is subject to a terminal disclaimer.

(21) Appl. No.: 11/701,632

(22) Filed: Feb. 2, 2007
(Under 37 CFR 1.47)

(65) Prior Publication Data
US 2008/0085909 A1 Apr. 10, 2008

Related U.S. Application Data

(60) Provisional application No. 60/774,492, filed on Feb. 17, 2006.

(51) Int. Cl.
C07D 473/18 (2006.01)
A61K 31/522 (2006.01)
A61P 19/02 (2006.01)
A61P 11/06 (2006.01)
A61P 35/00 (2006.01)
A61P 37/06 (2006.01)
A61P 31/10 (2006.01)
C07D 471/14 (2006.01)
C07D 239/50 (2006.01)
C07D 239/48 (2006.01)

(52) U.S. Cl. ........... 514/263.2; 514/263.22; 514/263.23; 514/263.37; 544/230; 544/276; 544/323; 544/326; 546/119; 546/279.1; 546/276.4

(58) Field of Classification Search ........... 514/263.2, 514/263.22, 263.23, 263.37; 544/230, 276
See application file for complete search history.

(56) References Cited

U.S. PATENT DOCUMENTS

| 4,247,556 | A | 1/1981 | von Bebenburg et al. |
| 4,813,998 | A | 3/1989 | Van Lommen et al. |
| 5,493,011 | A | 2/1996 | Jung et al. |
| 5,705,625 | A | 1/1998 | Civin et al. |
| 5,916,792 | A | 6/1999 | Civin et al. |
| 6,313,129 | B1 | 11/2001 | Uckun et al. |
| 6,372,740 | B1 * | 4/2002 | Murata et al. ............. 514/234.2 |
| 6,432,947 | B1 | 8/2002 | Arnaiz et al. |
| 6,452,005 | B1 | 9/2002 | Uckun et al. |
| 6,506,738 | B1 | 1/2003 | Yu et al. |
| 6,582,357 | B2 | 6/2003 | Ouchi et al. |
| 2004/0116435 | A1 | 6/2004 | Eriksson et al. |
| 2004/0116449 | A1 | 6/2004 | Changelian |
| 2004/0157739 | A1 | 8/2004 | Ahrens et al. |
| 2005/0032725 | A1 | 2/2005 | Rao et al. |
| 2007/0021443 | A1 | 1/2007 | Ohlmeyer et al. |
| 2007/0253896 | A1 | 11/2007 | Le Brazidec et al. |
| 2008/0085898 | A1 * | 4/2008 | Lu et al. ............. 514/234.2 |
| 2008/0119496 | A1 * | 5/2008 | Ohlmeyer et al. ....... 514/263.21 |
| 2008/0207613 | A1 | 8/2008 | Styles et al. |
| 2008/0214580 | A1 * | 9/2008 | Neagu et al. ............. 514/263.2 |
| 2008/0220256 | A1 | 9/2008 | Bhattacharya et al. |
| 2008/0254029 | A1 * | 10/2008 | Yanni et al. ............. 424/133.1 |
| 2008/0287468 | A1 * | 11/2008 | Ohlmeyer et al. ......... 514/263.2 |
| 2009/0023723 | A1 * | 1/2009 | Cole et al. ............. 514/234.2 |
| 2009/0069289 | A1 * | 3/2009 | Neagu et al. ............. 514/210.21 |
| 2009/0281075 | A1 * | 11/2009 | Roughton et al. ........ 514/210.21 |
| 2010/0093998 | A1 * | 4/2010 | Isobe et al. ............. 544/276 |
| 2010/0099870 | A1 * | 4/2010 | Isobe et al. ............. 544/276 |
| 2010/0120799 | A1 * | 5/2010 | Lazarides et al. ........ 514/263.23 |
| 2010/0130491 | A1 * | 5/2010 | Bonnert et al. ............. 514/234.2 |
| 2011/0046131 | A1 * | 2/2011 | Neagu et al. ............. 514/234.2 |

FOREIGN PATENT DOCUMENTS

| CA | 2238689 | 5/1997 |
| DE | 2841209 | 4/1979 |
| DE | 10 2005 042742 | 3/2007 |
| EP | 0 277 384 | 8/1988 |
| EP | 0 807 629 | 11/1997 |
| EP | 1043324 | 10/2000 |
| EP | 1221444 | 7/2002 |
| JP | 07075798 | 3/1995 |

(Continued)

OTHER PUBLICATIONS

Bakavoli, M., Journal of Sciences, Islamic Republic of Iran (1995), 6(3), 158-162.*

(Continued)

*Primary Examiner* — Mark Berch
(74) *Attorney, Agent, or Firm* — Knobbe, Martens, Olson & Bear LLP

(57) ABSTRACT

A chemical genus of purinones and 1H-imidazopyridinones, which are useful as PKCθ. inhibitors, and their methods of use are disclosed. The genus is represented by the formula I:

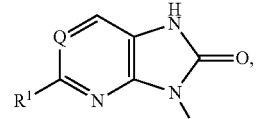

wherein
$R^1$ is chosen from nitrogen-attached heterocyclyl, nitrogen-attached substituted heterocyclyl wherein the point of attachment is a nitrogen heteroatom, and

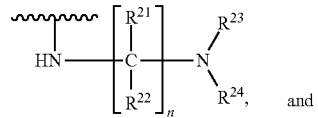

$R^2$ is chosen from aryl, substituted aryl, arylalkyl, substituted arylalkyl, heteroaryl, substituted heteroaryl, hetroarylalkyl, and substituted heteroarylalkyl.
A representative example is:

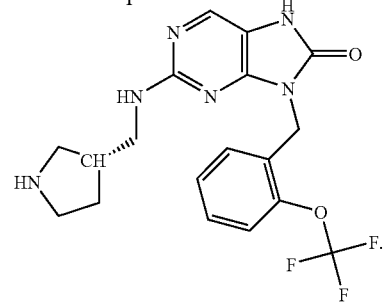

19 Claims, No Drawings

FOREIGN PATENT DOCUMENTS

| | | |
|---|---|---|
| JP | 2004 217582 | 8/2004 |
| WO | 99/41248 | 8/1999 |
| WO | 00/12089 | 3/2000 |
| WO | 01/19828 | 3/2001 |
| WO | WO 02/055521 | 7/2002 |
| WO | 03/051277 | 6/2003 |
| WO | 2004/043386 | 5/2004 |
| WO | 2004/099204 | 11/2004 |
| WO | WO 2005/023761 | 3/2005 |
| WO | 2005/066156 | 7/2005 |
| WO | 2006/069080 | 6/2006 |
| WO | WO 2006/074985 | 7/2006 |
| WO | WO 2006/087538 | 8/2006 |
| WO | WO 2006/091737 | 8/2006 |
| WO | 2006/096270 | 9/2006 |
| WO | 2006/108103 | 10/2006 |
| WO | 2007/035873 | 3/2007 |
| WO | WO 2007/058990 | 5/2007 |
| WO | WO 2007/140222 | 12/2007 |
| WO | WO 2007/146712 | 12/2007 |
| WO | WO 2008/043019 | 4/2008 |
| WO | WO 2008/043031 | 4/2008 |
| WO | WO 2008/051493 | 5/2008 |
| WO | WO 2008/051494 | 5/2008 |
| WO | WO 2008060301 A1 * | 5/2008 |
| WO | WO 2008/075196 | 6/2008 |
| WO | WO 2008143674 A1 * | 11/2008 |
| WO | WO 2008/152099 | 12/2008 |
| WO | WO 2009/062059 | 5/2009 |

OTHER PUBLICATIONS

Cetkovic-Cvrlje et al., "Targeting Janus kinase 3 in the treatment of leukemia and inflammatory diseases," *Arch. Immunol. Ther. Exp.*, vol. 52, pp. 69-82 (2004.).
Ortmann et al., "Janus kinases and signal transducers and activators of transcription: their roles in cytokine signaling, development and immunoregulation," *Arthritis Res.*, vol. 2, pp. 16-32 (2000).
Yamaoka et al., "The Janus kinases (Jaks)," *Genome Biology*, vol. 5:253, pp. 253.1-253.6 (2004).
Uckun et al., "Structure-based Design of Novel Anticancer Agents," *Current Cancer Drug Targets*, vol. 1(1), pp. 59-71 (2001).
Kawahara et al., "Critical role of the interleukin 2 (IL-2) receptor γ-chain associated Jak3 in the IL-2-induced c-*fos* and c-*myc*, but not *bcl*-2, gene induction," *Proc. Natl. Acad. Sci.*, vol. 92, pp. 8724-8728 (1995).
O'Shea et al., "A New Modality for Immunosuppression: Targeting the Jak/Stat Pathway," *Nature Reviews*, vol. 3, pp. 555-564 (2004).
Papageorgiou et al., "Is Jak3 a new drug target for immunomodulation-based therapies?" *TRENDS in Pharmacological Sciences*, vol. 25(11), pp. 558-562 (2004).
Lin et al., "Constitutive Activation of Jak3/Stat3 in Colon Carcinoma Tumors and Cell Lines", *American Journal of Pathology*, vol. 167(4), pp. 969-980 (2005).
Dana et al, "Role of Immunity and Inflammation in Corneal and Ocular Surface Disease Associated with Dry Eye," *Lacrimal Gland, Tear Film and Dry Eye Syndromes 3*, pp. 729-738 (2002).
Nagelhout et al., "Preservation of Tear Film Integrity and Inhibition of Corneal Injury by Dexamethasone in a Rabbit Model of Lacrimal Gland Inflammation-Induced Dry Eye," *Journal of Ocular Pharmacology and Therapeutics*, vol. 21(2), pp. 139-148 (2005).
Pflugfelder, S., "Perspective Anti-inflammatory Therapy for Dry Eye," *American Journal of Ophthalmology*, vol. 137(2), pp. 337-342 (2004).
Amin et al., "Inhibition of Jak3 induces apoptosis and decreases anaplastic lymphoma kinase activity in anaplastic large cell lymphoma," *Oncogene*, vol. 22, pp. 5399-5407 (2003).
Frantz, S., "Playing Dirty", *Nature*, vol. 437, pp. 942-943 (2005).
Lai et al., "Jak3 activation is significantly associated with ALK expression in anaplastic large cell lymphoma," *Human Pathology*, vol. 36, pp. 939-944 (2005).
Beijersbergen van Henegouwen GM et al., Hydrolysis of RRR0alpha-tocopheryl acetate (vitamin # acetate) in the skin and its UV protecting activity (an in vivo study with the rat) *J Photochem Photobiol*, Jul. 29, 2005, vol. 1, pp. 45-51.
Cadena-Amaro et al., Bioorganic & Medicinal Chemistry Letters, 2005, vol. 15, Issue 4, pp. 1069-1073.
Chem Abstracts Search #1 1996:496070 CAPLUS: Bakavoli et al., Synthesis of 4,5'-bis-pyrimidines and some related bis-fused pyrimidines, Journal of Sciences, Islamic Republic of Iran (1995), 6(3), 158-162.
Chem Abstracts Search #2 1980:604652 CAPLUS: Brazilian patent No. BR 7806210, Apr. 1, 1980.
Frankowski, Synthesis of imidazo [4,5-c][1,2]diazepine systems and their ribonucleosides, Tetrahedron, 1986, vol. 42, Issue 5, pp. 1511-1528.
Gaulon et al., A General and Facile Route to New Trisubstituted Purin-8-ones, Synthesis, Jul. 2005, p. 2227.
International Search Report dated Mar. 20, 2009 in International Application No. PCT/US2008/082832, filed Nov. 7, 2008.
Lum et al., 2,5-Diaminopyrimidines and 3,5-disubstituted azapurines as hinhibitors of glycogen synthase kinase-3 (GSK-3), Bioorganic & Medicinal Chemistry Letters, 2008, vol. 18, Issue 12, pp. 3578-3581.
Pochet et al., Construction of a self-complementary nucleoside from deoxyguanosine, Comptes Rendus de l'Academie des Sciences, Serie III: Sciences de la Vie, 1996, vol. 319, Issue 1, pp. 1-7.
Rokos et al., 8.2-Anhydro-8-Hydroxypurine αD-Ribosides, J. Carbohydrates, Nucleosides, Nucleotides, 1976, vol. Issue 77-91.
International Search Report dated Jan. 9, 2007 in International Application No. PCT/US2006/036833, filed Sep. 21, 2006.
International Search Report dated Jan. 7, 2010 in International Application No. PCT/US2009/048062, filed Jun. 19, 2009.
International Search Report from International Application No. PCT/US2007/080447, 2008.
International Search Report from International Application No. PCT/US2007/080464, 2008.
Cetkovic-Cvrlje et al., "Dual Targeting of Burton's Tyrosine Kinase and Janus Kinase 3 with Rationally Designed Inhibitors Prevents Graft-Versus-Host Disease (GVHD)," *British Journal of Haematology*, vol. 126, pp. 821-827 (2004).
Changelian et al., "Prevention of Organ Allograft Rejection by a Specific Janus Kinase 3 Inhibitor," *Science*, vol. 302, pp. 875-878 (2003).
O'Shea, J.J., "Cytokine signaling: new insights and new opportunities for therapeutic intervention?", *Arthristis Res.*, vol. 3(Suppl A): L018 (2001).
Harrington et al., "VX-680, a potent and selective small-molecule inhibitor of the Aurora kinases, suppresses tumor growth in vivo," *Nature Medicine*, vol. 10(3), pp. 262-267 (2004).
Jung et al., "Discovery of Novel and Potent Thiazoloquinazolines as Selective Aurora A and B Kinase," American Chem Soc., pp. 1-16 (2005).
Martinez-Lostao et al., "Role of the STAT1 pathway in apoptosis induced by fludarabine and JAK kinase inhibitors in B-cell chronic lymphocytic leukemia," *Leuk Lymphoma*, vol. 46(3), pp. 435-442 (2005), Abstract only (PMID: 15621835).
Pearson, H., "Designer transplant drug shows promise in monkeys," *News & Nature* (2003).
Goldberg et. al., "Optimization of 2-Phenylaminoimidazo [4,5-*h*]isoquinolin-9-ones: Orally Active Inhibitors of Ick Kinase," *Journal of Medical Chem.*, vol. 46, pp. 1337-1349, 2003.
International Search Report from International Application No. PCT/US2006/012824, 2007.
International Search Report from International Application No. PCT/US2006/061004, 2007.
International Search Report and Written Opinion from International Application No. PCT/US2007/081232, 2008.
International Search Report and Written Opinion from International Application No. PCT/US2007/069530, 2008.
Hirota et all, "Synthesis and Biological Evaluation of 2,8-Disubstituted 9-Benzyladenines: Discovery of 8-Mercaptoadenines as Potent Interferon-Inducers," *Bioorganic & Medicinal Chemistry 11*, 2003, pp. 2715-2722.
Written Opinion corresponding to PCT/US2007/080447, 2008.
Written Opinion corresponding to PCT/US2007/080464, 2008.
Written Opinion corresponding to PCT/US2006/012824, 2007.
Written Opinion corresponding to PCT/US2006/061004, 2007.

* cited by examiner

PURINONES AND 1H-IMIDAZOPYRIDINONES AS PKC-THETA INHIBITORS

CROSS-REFERENCE TO RELATED APPLICATIONS

This application claims benefit of priority to U.S. Provisional Application No. 60/774,492 filed Feb. 17, 2006, which is incorporated herein by reference in its entirety.

FIELD OF THE INVENTION

The present invention relates to a chemical genus of purinones and 1H-imidazopyridinones which are useful as PKCθ inhibitors.

BACKGROUND OF THE INVENTION

Members of the protein kinase C (PKC) family of serine/threonine kinases play critical roles in the regulation of cellular differentiation and proliferation of diverse cell types. Ten mammalian members of PKC family have been identified and designated α, β, γ, δ, ε, ζ, η, θ, μ, and λ. The predicted structure of PKCθ displays the highest homology with members of the $Ca^{2+}$ independent novel PKC subfamily, including PKCδ, ε, and η. PKCθ is most highly related to PKCδ.

PKCθ is expressed predominantly in lymphoid tissue and skeletal muscle. It has been shown that PKCθ is essential for T-cell receptor (TCR)-mediated T-cell activation but inessential during TCR-dependent thymocyte development. PKCθ, but not other PKC isoforms, translocates to the site of cell contact between antigen-specific T-cells and antigen presenting cells (APC), where it localizes with the TCR in the central core of the T-cell activation. PKCθ, but not the α, ε, or ζ isoenzymes, selectively activated a FasL promoter-reporter gene and upregulated the mRNA or cell surface expression of endogenous FasL. On the other hand, PKCθ and ε promoted T-cell survival by protecting the cells from Fas-induced apoptosis, and this protective effect was mediated by promoting p90Rsk-dependent phosphorylation of BAD. Thus, PKCθ appears to play a dual regulatory role in T-cell apoptosis.

The selective expression of PKCθ in T-cells and its essential role in mature T-cell activation establish that PKCθ inhibitors are useful for the treatment or prevention of disorders or diseases mediated by T lymphocytes, for example, autoimmune disease such as rheumatoid arthritis and lupus erythematosus, and inflammatory disease such as asthma and inflammatory bowel diseases.

PKCθ is identified as a drug target for immunosuppression in transplantation and autoimmune diseases (Isakov et al. (2002) Annual Review of Immunology, 20, 761-794). PCT Publication WO2004/043386 identifies PKCθ as a target for treatment of transplant rejection and multiple sclerosis. PKCθ also plays a role in inflammatory bowel disease (The Journal of Pharmacology and Experimental Therapeutics (2005), 313 (3), 962-982), asthma (WO 2005062918), and lupus (Current Drug Targets: Inflammation & Allergy (2005), 4 (3), 295-298).

In addition, PKCθ is highly expressed in gastrointestinal stromal tumors (Blay, P. et al. (2004) Clinical Cancer Research, 10, 12, Pt. 1), it has been suggested that PKCθ is a molecular target for treatment of gastrointestinal cancer (Wiedmann, M. et al. (2005) Current Cancer Drug Targets 5(3), 171). Thus, small molecule PKCθ inhibitors can be useful for treatment of gastrointestinal cancer.

Experiments conduced in PKCθ knock-out mice led to the conclusion that PKCθ inactivation prevented fat-induced defects in insulin signalling and glucose transport in skeletal muscle (Kim J. et al, 2004, The J. of Clinical Investigation 114 (6), 823). This data suggests that PKCθ is a potential therapeutic target for the treatment of type 2 diabetes, and hence small molecule PKCθ inhibitors can be useful for treating such disease.

Therefore, PKCθ inhibitors are useful in treatment of T-cell mediated diseases including autoimmune diseases such as rheumatoid arthritis, lupus erythematosus, and multiple sclerosis and inflammatory diseases such as asthma and inflammatory bowel disease. In addition, PKCθ inhibitors are useful in treatment of transplant rejection, gastrointestinal cancer, and diabetes.

SUMMARY OF THE INVENTION

In one aspect the invention relates to compounds of the formula I:

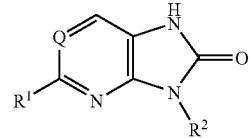

wherein:
Q is chosen from N and CH;
$R^1$ is chosen from nitrogen-attached heterocyclyl, substituted nitrogen-attached heterocyclyl and

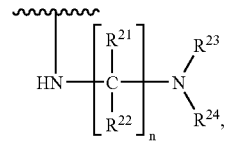

wherein
n is an integer from 2 to 6;
$R^{21}$ is chosen separately in each occurrence from —H, $C_1$-$C_4$ alkyl and —OH;
$R^{22}$ is chosen separately in each occurrence from —H, $C_1$-$C_4$ alkyl and a bond to $R^{24}$;
$R^{23}$ is chosen from —H, $C_1$-$C_4$ alkyl and a bond to $R^{24}$;
$R^{24}$ is chosen from —H, $C_1$-$C_4$ alkyl or together with either of $R^{22}$ or $R^{23}$ forms a 5-7 membered nitrogen heterocycle optionally substituted with $C_1$-$C_4$ alkyl; and
$R^2$ is chosen from aryl, substituted aryl, arylalkyl, substituted arylalkyl, heteroaryl, substituted heteroaryl, hetroarylalkyl, and substituted heteroarylalkyl.

In another aspect the invention relates to pharmaceutical compositions comprising a pharmaceutically acceptable carrier and a compound of formula I, or salt thereof.

In another aspect the invention relates to a method for treating T-cell mediated diseases including autoimmune diseases such as rheumatoid arthritis, lupus erythematosus, and multiple sclerosis, inflammatory diseases such as asthma and inflammatory bowel disease, transplant rejection, gastrointestinal cancer, and diabetes. The method comprises administering a therapeutically effective amount of a compound of formula I, or salt thereof.

DETAILED DESCRIPTION OF THE INVENTION

In its broadest sense, the invention relates to compounds of the formula I, or salt thereof:

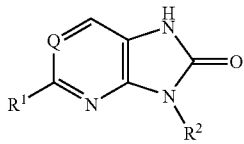

(I)

wherein:

Q is chosen from N and CH;

$R^1$ is chosen from nitrogen-attached heterocyclyl, substituted nitrogen-attached heterocyclyl and

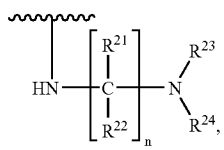

wherein n is an integer from 2 to 6;

$R^{21}$ is chosen separately in each occurrence from —H, $C_1$-$C_4$ alkyl and —OH;

$R^{22}$ is chosen separately in each occurrence from —H, $C_1$-$C_4$ alkyl and a bond to $R^{24}$;

$R^{23}$ is chosen from —H, $C_1$-$C_4$ alkyl and a bond to $R^{24}$;

$R^{24}$ is chosen from —H, $C_1$-$C_4$ alkyl or together with either of $R^{22}$ or $R^{23}$ forms a 5-7 membered nitrogen heterocycle optionally substituted with $C_1$-$C_4$ alkyl; and $R^2$ is chosen from aryl, substituted aryl, arylalkyl, substituted arylalkyl, heteroaryl, substituted heteroaryl, hetroarylalkyl, and substituted heteroarylalkyl.

In the description of $R^1$, when $R^1$ is

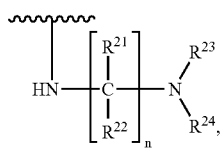

the terminology "$R^{21}$ is chosen separately in each occurrence from —H, $C_1$-$C_4$ alkyl and —OH," and "$R^{22}$ is chosen separately in each occurrence from —H, $C_1$-$C_4$ alkyl" is intended to mean that when n is 3, for example, then $R^1$ may be

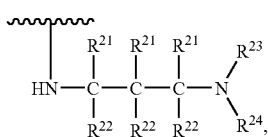

where each occurrence of $R^{21}$ and each occurrence of $R^{22}$ is chosen among the recited possibilities, such as:

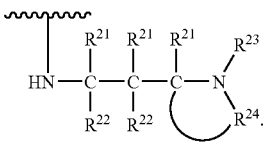

for example. Furthermore, in the definition of $R^1$, when it is said that $R^{22}$ may be a bond to $R^{24}$, when n is 3, for example, then $R^1$ may be

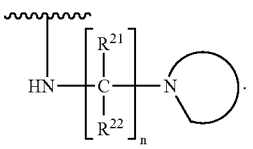

Similarly, in the definition of $R^1$, when it is said that $R^{23}$ may be a bond to $R^{24}$, then $R^1$ may be

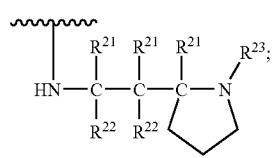

The following structures are exemplary of compounds in which $R^{24}$ together with either of $R^{22}$ or $R^{23}$ forms a 5-7 membered nitrogen heterocycle:

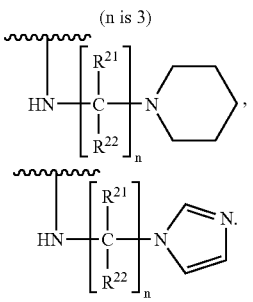

In one embodiment, $R^1$ is chosen from

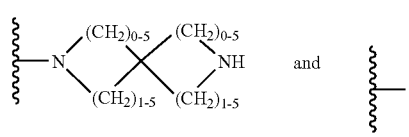

wherein $R^9$ is chosen from amino($C_1$-$C_6$)alkyl, ($C_1$-$C_6$)alkylamino($C_1$-$C_6$)alkyl and di[($C_1$-$C_6$)alkyl]amino($C_1$-$C_6$)alkyl.

In another embodiment, $R^1$ is

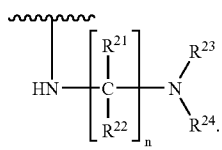

In another embodiment, $R^{22}$ is chosen separately in each occurrence from —H and $C_1$-$C_4$ alkyl; and $R^{24}$ together with $R^{23}$ forms a 5-7 membered nitrogen heterocycle optionally substituted with $C_1$-$C_4$ alkyl.

In another embodiment, $R^{22}$ is chosen separately in each occurrence from —H and $C_1$-$C_4$ alkyl; $R^{23}$ is chosen from —H, $C_1$-$C_4$ alkyl; and $R^{24}$ is —H or $C_1$-$C_4$ alkyl.

In another embodiment, $R^{22}$ is chosen separately in each occurrence from H, $C_1$-$C_4$ alkyl and a bond to $R^{24}$; $R^{23}$ is chosen from H, $C_1$-$C_4$ alkyl; and $R^{24}$ together with one occurrence of $R^{22}$ forms a 5-7 membered nitrogen heterocycle optionally substituted with $C_1$-$C_4$ alkyl.

In another embodiment, $R^2$ is chosen from,

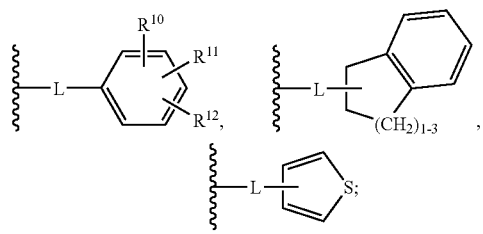

wherein
$R^{10}$, $R^{11}$, and $R^{12}$ are independently chosen from —H, halogen, —OCH$_3$, —OCF$_3$, —CF$_3$, $C_1$-$C_4$ alkyl, and phenyl; and
L is a $C_0$-$C_{10}$ alkyl.

In another embodiment,
$R^2$ is chosen from

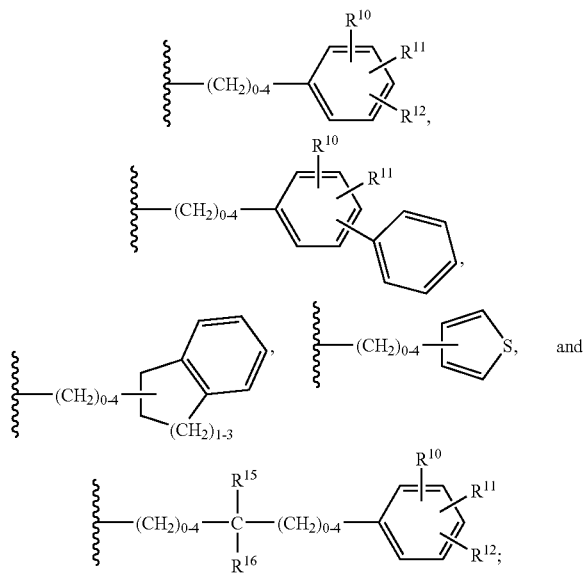

wherein
$R^{10}$, $R^{11}$, and $R^{12}$ are independently chosen from —H, halogen, —OCH$_3$, —OCF$_3$, —CF$_3$, and $C_1$-$C_4$ alkyl; and
$R^{15}$ and $R^{16}$ are independently chosen from —H and $C_1$-$C_4$ alkyl.

In a narrower embodiment, the invention relates to compounds of the formula I, or salt thereof:
wherein:

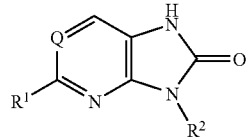

Q is chosen from N and CH;

$R^1$ is chosen from

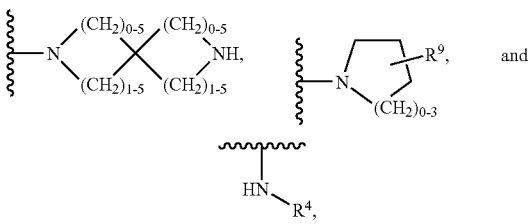

wherein
$R^4$ is chosen from

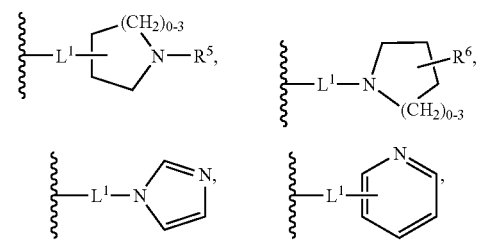

and -M-NR$^7$R$^8$;
wherein
$R^5$, $R^6$, and $R^9$ are independently chosen from —H, $C_1$-$C_4$ alkyl, —OH, —OCH$_3$, halogen, and aminoalkyl;
$R^7$ and $R^8$ are independently chosen from —H, $C_1$-$C_4$ alkyl, and aminoalkyl;
$L^1$ is a $C_0$-$C_{10}$ alkyl optionally substituted with —OH, with a proviso that —OH cannot be bonded to a carbon atom that is also bonded to N;
M is $C_2$-$C_{10}$ alkyl optionally substituted with —OH, with a proviso that —OH cannot be bonded to a carbon atom that is also bonded to N; and $R^2$ is chosen from,

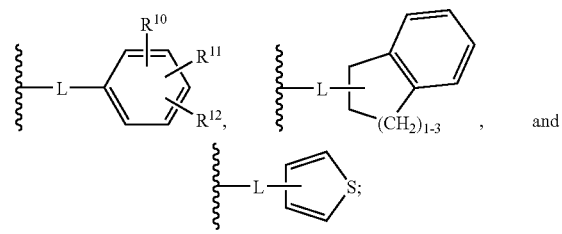

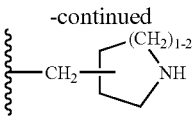

wherein
$R^{10}$, $R^{11}$, and $R^{12}$ are independently chosen from —H, halogen, —OCH$_3$, —OCF$_3$, —CF$_3$, C$_1$-C$_4$ alkyl, and phenyl.

L is a C$_0$-C$_{10}$ alkyl.

In another embodiment,
$R^4$ is chosen from

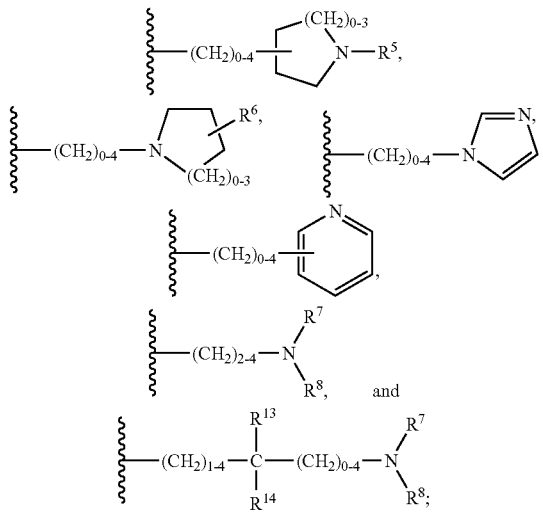

wherein
$R^5$, $R^6$, and $R^9$ are independently chosen from —H, C$_1$-C$_4$ alkyl, —OH, —OCH$_3$, halogen, and aminoalkyl;
$R^7$ and $R^8$ are independently chosen from —H, C$_1$-C$_4$ alkyl, and aminoalkyl; and
$R^{13}$ and $R^{14}$ are independently chosen from —H, —OH, and C$_1$-C$_4$ alkyl, with a proviso that —OH cannot be bonded to a carbon atom that is also bonded to N.

In another embodiment,
$R^5$, $R^6$, $R^7$, and $R^8$ are independently chosen from —H and C$_1$-C$_4$ alkyl;
$R^9$ is —$R^{17}$—NR$^7$R$^8$;
wherein
$R^{17}$ is a C$_1$-C$_4$ alkyl.

In another embodiment,
$R^4$ is chosen from

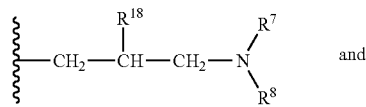
and wherein
$R^7$ and $R^8$ are independently chosen from —H and —CH$_3$; and
$R^{18}$ is chosen from —H and —OH.

In another embodiment,
$R^2$ is chosen from

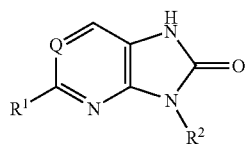

wherein
$R^{10}$, $R^{11}$, and $R^{12}$ are independently chosen from —H, halogen, —OCH$_3$, —OCF$_3$, —CF$_3$, and C$_1$-C$_4$ alkyl; and
$R^{15}$ and $R^{16}$ are independently chosen from —H and C$_1$-C$_4$ alkyl.

In yet another embodiment, the invention relates to compounds of the formula I, or salt thereof:
wherein:

(I)

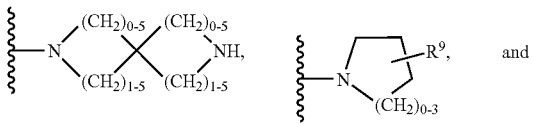

Q is chosen from N and CH;
$R^1$ is chosen from

-continued

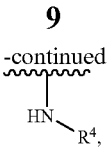

wherein
R⁴ is chosen from

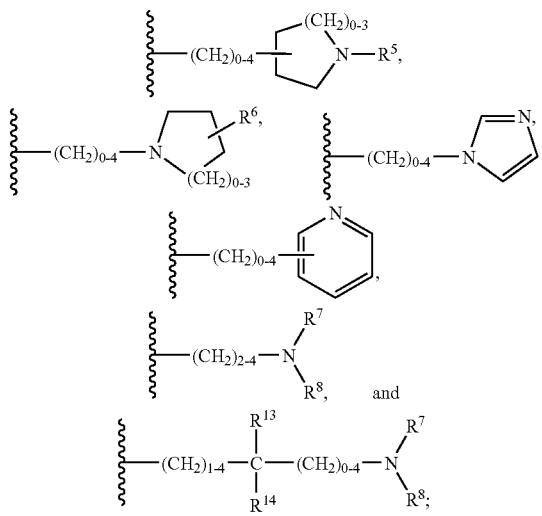

wherein
R⁵, R⁶, and R⁹ are independently chosen from —H, $C_1$-$C_4$ alkyl, —OH, —OCH₃, halogen, and aminoalkyl;
R⁷ and R⁸ are independently chosen from —H, $C_1$-$C_4$ alkyl, and aminoalkyl; and
R¹³ and R¹⁴ are independently chosen from —H, —OH, and $C_1$-$C_4$ alkyl, with a proviso that —OH cannot be bonded to a carbon atom that is also bonded to N;
R² is chosen from,

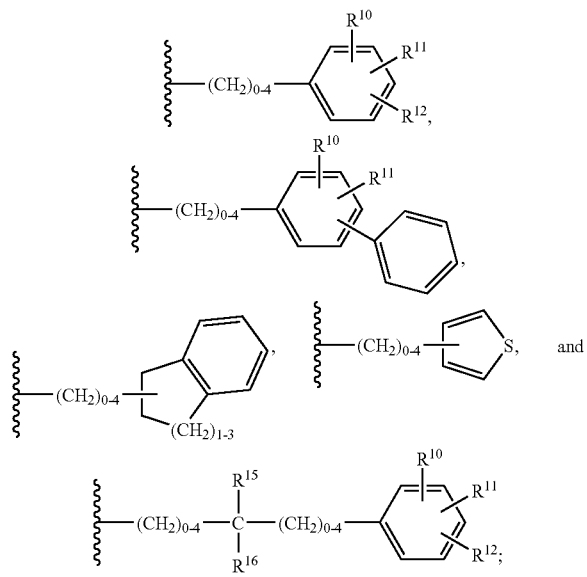

wherein
R¹⁰, R¹¹, and R¹² are independently chosen from —H, halogen, —OCH₃, —OCF₃, —CF₃, and $C_1$-$C_4$ alkyl; and
R¹⁵ and R¹⁶ are independently chosen from —H and $C_1$-$C_4$ alkyl.

In another embodiment,
R⁵, R⁶, R⁷, and R⁸ are independently chosen from —H and $C_1$-$C_4$ alkyl;
R⁹ is —R¹⁷—NR⁷R⁸;
wherein
R¹⁷ is a $C_1$-$C_4$ alkyl.

In another embodiment,
R⁴ is chosen from

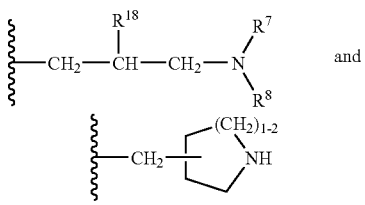

wherein
R⁷ and R⁸ are independently chosen from —H and —CH₃; and
R¹⁸ is chosen from —H and —OH.

In another embodiment, Q is N. In yet another embodiment, Q is CH.

In one embodiment, the invention is directed to a method of treatment of a T-cell mediated disease comprising administering a therapeutically effective amount of a compound of formula I, or salt thereof. The T-cell mediated disease may be, for example, an autoimmune disease or an inflammatory disease. The autoimmune disease, may be, for example, rheumatoid arthritis or lupus erythematosus. The inflammatory disease may be, for example, asthma or inflammatory bowel disease.

In another embodiment, the invention is directed to a method of treatment of cancer, such as gastrointestinal cancer, comprising administering a therapeutically effective amount of a compound of formula I, or salt thereof.

In yet another embodiment, the invention is directed to a method of treatment of diabetes comprising administering a therapeutically effective amount of a compound of formula I, or salt thereof.

Definitions

Throughout this specification the terms and substituents retain their definitions.

Alkyl and alkane are intended to include linear, branched, or cyclic hydrocarbon structures and combinations thereof. Lower alkyl refers to alkyl groups of from 1 to 6 carbon atoms. Examples of lower alkyl groups include methyl, ethyl, propyl, isopropyl, butyl, s- and t-butyl and the like. Preferred alkyl groups are those of $C_{20}$ or below. Cycloalkyl is a subset of alkyl and includes cyclic hydrocarbon groups of from 3 to 8 carbon atoms. Examples of cycloalkyl groups include c-propyl, c-butyl, c-pentyl, norbornyl and the like.

($C_1$ to $C_n$)Hydrocarbon includes alkyl, cycloalkyl, alkenyl, alkynyl, aryl and combinations thereof containing only hydrogen and one to n carbons. Examples include vinyl, allyl, cyclopropyl, propargyl, phenethyl, cyclohexylmethyl, camphoryl and naphthylethyl. Saturated ($C_1$ to $C_n$)hydrocarbon is identical in meaning to ($C_1$ to $C_n$)alkyl or ($C_1$ to $C_n$)alkane as used herein. Whenever reference is made to $C_{0-n}$ alkyl, ($C_0$ to $C_n$)alkyl, or ($C_0$ to $C_n$)alkane when number of carbon atoms is 0, a direct bond is implied.

Alkoxy or alkoxyl refers to groups of from 1 to 8 carbon atoms of a straight, branched, cyclic configuration and combinations thereof attached to the parent structure through an oxygen. Examples include methoxy, ethoxy, propoxy, isopropoxy, cyclopropyloxy, cyclohexyloxy and the like. Loweralkoxy refers to groups containing one to four carbons.

Fluoroalkyl refers to alkyl residues in which one or more hydrogens have been replaced by fluorine. It includes perfluoroalkyl, in which all the hydrogens have been replaced by fluorine. Examples include fluoromethyl, difluoromethyl, trifluoromethyl, trifluoroethyl and pentafluoroethyl.

Oxaalkyl refers to alkyl residues in which one or more carbons (and their associated hydrogens) have been replaced by oxygen. Examples include methoxypropoxy, 3,6,9-trioxadecyl and the like. The term oxaalkyl is intended as it is understood in the art [see *Naming and Indexing of Chemical Substances for Chemical Abstracts*, published by the American Chemical Society, ¶196, but without the restriction of ¶127(a)], i.e. it refers to compounds in which the oxygen is bonded via a single bond to its adjacent atoms (forming ether bonds); it does not refer to doubly bonded oxygen, as would be found in carbonyl groups. Similarly, thiaalkyl and azaalkyl refer to alkyl residues in which one or more carbons has been replaced by sulfur or nitrogen, respectively. Examples include ethylaminoethyl and methylthiopropyl.

Acyl refers to groups of from 1 to 8 carbon atoms of a straight, branched, cyclic configuration, saturated, unsaturated and aromatic and combinations thereof, attached to the parent structure through a carbonyl functionality. One or more carbons in the acyl residue may be replaced by nitrogen, oxygen or sulfur as long as the point of attachment to the parent remains at the carbonyl. Examples include acetyl, benzoyl, propionyl, isobutyryl, t-butoxycarbonyl, benzyloxycarbonyl and the like. Lower-acyl refers to groups containing one to four carbons.

Aryl and heteroaryl mean a 5- or 6-membered aromatic or heteroaromatic ring containing 0-3 heteroatoms selected from O, N, or S; a bicyclic 9- or 10-membered aromatic or heteroaromatic ring system containing 0-3 heteroatoms selected from O, N, or S; or a tricyclic 13- or 14-membered aromatic or heteroaromatic ring system containing 0-3 heteroatoms selected from O, N, or S. As commonly understood, when referring to aryl as a substituent, it is intended that the point of attachment is a ring carbon of the aryl group (or ring carbon or heteroatom of the heteroaryl). For the purpose of the present invention, aryl and heteroaryl refer to systems in which at least one ring, but not necessarily all rings, are fully aromatic. Thus aromatic 6- to 14-membered carbocyclic rings include, e.g., benzene, naphthalene, indane, tetralin, benzocycloheptane and fluorene and the 5- to 10-membered aromatic heterocyclic rings include, e.g., imidazole, pyridine, indole, isoindoline, thiophene, benzopyranone, thiazole, furan, benzimidazole, quinoline, isoquinoline, tetrahydroisoquinoline, quinoxaline, tetrahydrocarboline, pyrimidine, pyrazine, tetrazole and pyrazole.

Arylalkyl means an alkyl residue attached to an aryl ring. As commonly understood, when referring to arylalkyl as a substituent, it is intended that the point of attachment is the alkyl group. Examples of arylalkyl are benzyl, phenethyl, phenylpropyl and naphthylethyl. Heteroarylalkyl means an alkyl residue attached to a heteroaryl ring. Examples include, e.g., pyridinylmethyl, pyrimidinylethyl and the like.

Heterocycle means a cycloalkyl or aryl residue in which from one to three carbons is replaced by a heteroatom selected from the group consisting of N, O and S. The nitrogen and sulfur heteroatoms may optionally be oxidized, and the nitrogen heteroatom may optionally be quaternized. Heterocycles also include spiroheterocycles. It is to be noted that heteroaryl is a subset of heterocycle in which the heterocycle is aromatic. Examples of heterocyclyl residues additionally include piperazinyl, 4-piperidinyl, pyrazolidinyl, imidazolyl, imidazolinyl, imidazolidinyl, pyrazinyl, oxazolidinyl, isoxazolidinyl, thiazolidinyl, isothiazolyl, quinuclidinyl, isothiazolidinyl, benzimidazolyl, thiadiazolyl, benzopyranyl, benzothiazolyl, tetrahydrofuryl, tetrahydropyranyl, thienyl, benzothienyl, thiamorpholinyl, thiamorpholinylsulfoxide, thiamorpholinylsulfone, oxadiazolyl, triazolyl and tetrahydroquinolinyl.

Whenever reference is made to nitrogen attached heterocycle or nitrogen heterocycle, such heterocycle contains at least one nitrogen, but may also contain additional nitrogen atom(s) and/or other heteroatoms such as O and/or S.

Aminoalkyl means an amino group bound to a core structure via an alkyl group, e.g., aminomethyl, aminoethyl, aminopenthyl, etc. The alkyl group, as defined above, could be straight or branched and, therefore, an aminoalkyl includes, e.g., —$CH_2CH_2CH(CH_3)CH_2NH_2$, —$CH_2C(CH_3)_2CH_2NH_2$, etc. Alkylaminoalkyl means a secondary amine bound to a core structure via an alkyl group, e.g., —$CH_2CH_2NHCH_3$, —$CH2CH2CH_2NHCH_2CH_3$, etc. Dialkylaminoalkyl means a tertiary amine bound to a core structure via an alkyl group, e.g., —$CH_2N(CH_3)_2$, —$CH2CH2CH_2N(CH_3)CH_2CH_3$, etc.

Substituted alkyl, aryl, cycloalkyl, heterocyclyl etc. refer to alkyl, aryl, cycloalkyl, or heterocyclyl wherein up to three H atoms in each residue are replaced with loweralkyl, halogen, haloalkyl, hydroxy, hydroxymethyl, loweralkoxy, perfluoroloweralkoxy, carboxy, carboalkoxy (also referred to as alkoxycarbonyl), carboxamido (also referred to as alkylaminocarbonyl), sulfonamido, aminosulfonyl, alkylaminosulfonyl, cyano, carbonyl, nitro, amino, alkylamino, dialkylamino, ureido, alkylureido, mercapto, alkylthio, sulfoxide, sulfone, acylamino, amidino, phenyl, benzyl, heteroaryl, phenoxy, benzyloxy, or heteroaryloxy.

The term "halogen" means fluorine, chlorine, bromine or iodine.

As used herein, reference to "treatment" or "treating" a patient are intended to include prophylaxis. The terms include amelioration, prevention and relief from the symptoms and/or effects associated with these disorders. The terms "preventing" or "prevention" refer to administering a medicament beforehand to forestall or obtund an attack. Persons of ordinary skill in the medical art (to which the present method claims are directed) recognize that the term "prevent" is not an absolute term. In the medical art it is understood to refer to the prophylactic administration of a drug to diminish the likelihood or seriousness of a condition, and this is the sense intended.

ABBREVIATIONS

The following abbreviations and terms have the indicated meanings throughout:

Ac=acetyl
anh.=anhydrous
BNB=4-bromomethyl-3-nitrobenzoic acid
Boc=t-butyloxy carbonyl
Bu=butyl
CBZ=carbobenzoxy=benzyloxycarbonyl
CDI=carbonyl diimidazole
DBU=diazabicyclo[5.4.0]undec-7-ene
DCM=dichloromethane=methylene chloride=$CH_2Cl_2$ DEAD=diethyl azodicarboxylate
DIC=diisopropylcarbodiimide
DIEA=N,N-diisopropylethyl amine
DMAP=4-N,N-dimethylaminopyridine
DMF=N,N-dimethylformamide
DMSO=dimethyl sulfoxide
DVB=1,4-divinylbenzene
EEDQ=2-ethoxy-1-ethoxycarbonyl-1,2-dihydroquinoline
Et=ethyl
FCC=flash column chromography
Fmoc=9-fluorenylmethoxycarbonyl
GC=gas chromatography
HATU=O-(7-Azabenzotriazol-1-yl)-1,1,3,3-tetramethyluronium hexafluorophosphate
HOAc=acetic acid
HOBt=hydroxybenzotriazole
Me=methyl
mesyl=methanesulfonyl
MTBE=methyl t-butyl ether
NMO=N-methylmorpholine oxide
PEG=polyethylene glycol
Ph or □=phenyl
PhOH=phenol
PfP=pentafluorophenol
PPTS=pyridinium p-toluenesulfonate
PyBroP=bromo-tris-pyrrolidino-phosphonium hexafluorophosphate
rt=room temperature
sat'd=saturated
TBDMS=t-butyldimethylsilyl
TFA=trifluoroacetic acid
THF=tetrahydrofuran
TIPSO=triisopropylsilanyloxy
TMOF=trimethyl orthoformate
TMS=trimethylsilyl
tosyl=p-toluenesulfonyl
Trt=triphenylmethyl Although this invention is susceptible to embodiment in many different forms, preferred embodiments of the invention are shown. It should be understood, however, that the present disclosure is to be considered as an exemplification of the principles of this invention and is not intended to limit the invention to the embodiments illustrated.

It may be found upon examination that certain members of the claimed genus are not patentable to the inventors in this application. In this event, subsequent exclusions of species from the compass of applicants' claims are to be considered artifacts of patent prosecution and not reflective of the inventors' concept or description of their invention; the invention encompasses all of the members of the genus (I) that are not already in the possession of the public.

In general, the compounds of the present invention may be prepared by the methods illustrated in the general reaction schemes as, for example, described below, or by modifications thereof, using readily available starting materials, reagents and conventional synthesis procedures. In these reactions, it is also possible to make use of variants that are in themselves known, but are not mentioned here.

General Synthesis of Purinones

One method for preparing purinone analogs of the invention is shown in Scheme 1. Displacement of the two chlorides in 2,4-dichloro-5-nitropyrimidine 1 usually occurs in a regioselective manner. Thus, the more reactive chloride in the 4-position is first displaced by an amine R'NH$_2$ to yield compound 2. Addition of a second amine R"NH$_2$ displaces the chloride in the 2-position. Reduction of the nitro group in 3 to an amine using reagents well known in the art (e.g. Raney Ni/H$_2$, Fe/EtOH/aqAcOH, Na$_2$S$_2$O$_4$/NH$_4$OH/H$_2$O/Dioxane), followed by cyclization using, for example, carbonyldiimidazole gives purinone 5.

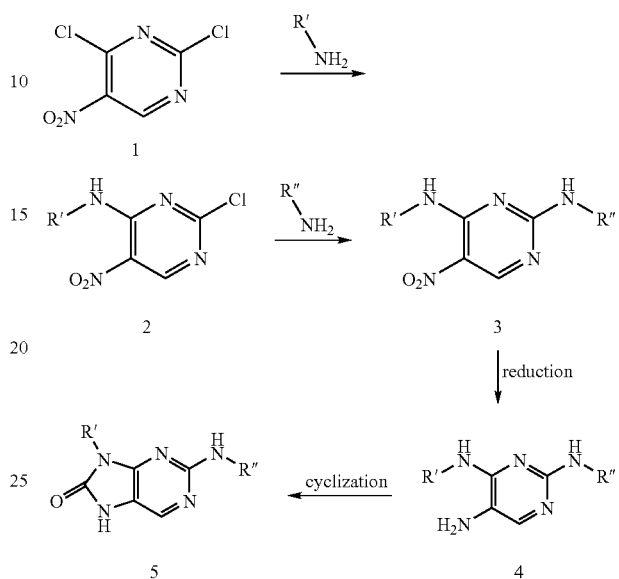

Scheme 1. Synthesis of purinone analogs.

The purinone analogs of the invention may be prepared on solid support (Scheme 2). For example, an acid cleavable linker can be attached to the ARGOGEL-NH$_2$ resin. The resin with the linker is first reductive aminated with a R'NH$_2$. The pyrimidine 2a, which is similarly prepared from the first step in Scheme 1, is then attached to the resin bound amine by a nucleophilic displacement reaction. Reduction of the nitro group, followed by ring closure with 4-nitrophenyl chloroformate, yields the purinone. The product can then be released from the solid support by treatment with acid such as trifloroacetic acid.

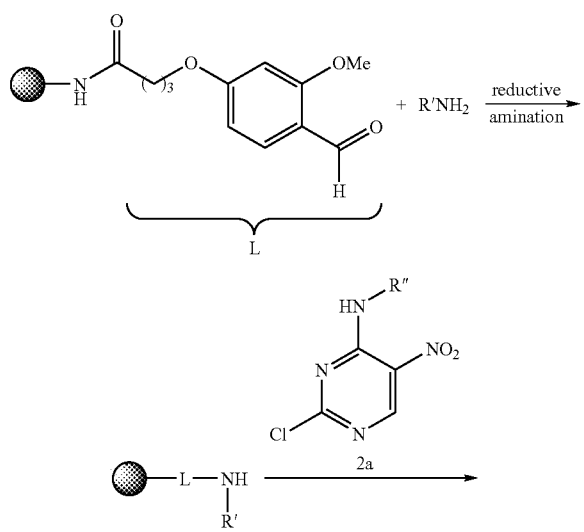

Scheme 2. Solid phase synthesis of purinone analogs.

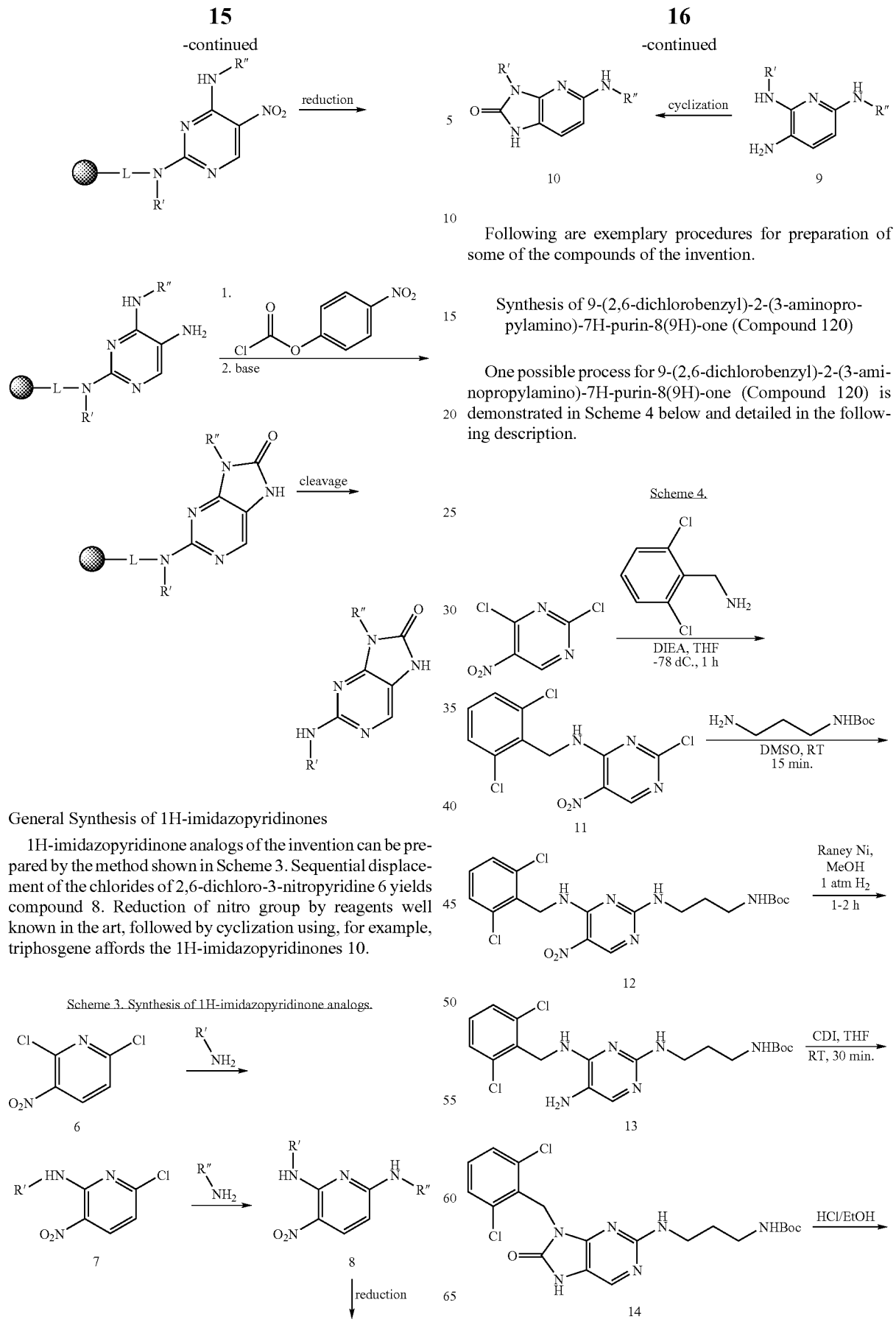

Following are exemplary procedures for preparation of some of the compounds of the invention.

Synthesis of 9-(2,6-dichlorobenzyl)-2-(3-aminopropylamino)-7H-purin-8(9H)-one (Compound 120)

One possible process for 9-(2,6-dichlorobenzyl)-2-(3-aminopropylamino)-7H-purin-8(9H)-one (Compound 120) is demonstrated in Scheme 4 below and detailed in the following description.

General Synthesis of 1H-imidazopyridinones 1H-imidazopyridinone analogs of the invention can be prepared by the method shown in Scheme 3. Sequential displacement of the chlorides of 2,6-dichloro-3-nitropyridine 6 yields compound 8. Reduction of nitro group by reagents well known in the art, followed by cyclization using, for example, triphosgene affords the 1H-imidazopyridinones 10.

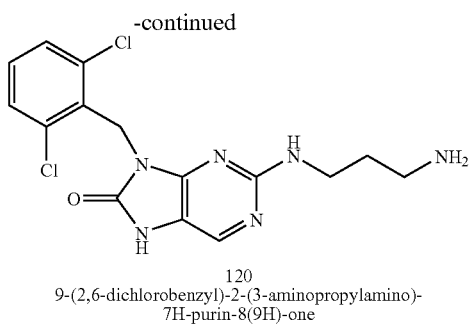

120
9-(2,6-dichlorobenzyl)-2-(3-aminopropylamino)-
7H-purin-8(9H)-one

N-(2,6-dichlorobenzyl)-2-chloro-5-nitropyrimidin-4-
amine (11)

A 500 mL round-bottom flask under argon atmosphere was charged with 2,4-dichloro-5-nitropyrimidine [5.0 g, 25.8 mmol] and dissolved in THF [30 mL, anh.]. The resulting solution was cooled to −78° C. A THF [25 mL, anh.] solution of 2,6-Dichlorobenzylamine [4.54 g, 25.8 mmol] and N,N-Diisopropylethylamine [9.9 mL, 56.7 mmol] was added dropwise over 20 minutes. The resulting off-white suspension was stirred at −78° C. for 50 minutes and the cooling bath was then removed. The mixture warmed slowly over 30 minutes before removal of the volatiles in vacuo. The crude yellow-orange solid was dissolved in minimal MeOH and DCM and applied to a slurry of silica gel. Elution with a gradient of MeOH (0-2%) in DCM gave a first fraction [4.116 g] comprising the title compound 11 and its regiosiomer (N-(2,6-dichlorobenzyl)-4-chloro-5-nitropyrimidin-2-amine) in a ratio of 3:7 by HPLC, followed by a second fraction [4.38 g] containing pure 11 only.

Data for N-(2,6-dichlorobenzyl)-2-chloro-5-nitropyrimidin-4-amine (11):
$^1$H NMR (300 MHz, CDCl$_3$): δ 9.08 (s, 1H), 8.67 (br s, 1H), 7.38 (d, 2H), 7.26 (t, 1H), 5.13 (d, 2H); MS (ESI) m/z 333.0/335.0 [M+H]$^+$; $\lambda_{max}$=224.3 nm, 257.3 nm, 285-340 nm tail.

Data for N-(2,6-dichlorobenzyl)-4-chloro-5-nitropyrimidin-2-amine (regioisomer): $\lambda_{max}$=219.6 nm, 319.0 nm.

tert-Butyl-3-(4-(2,6-dichlorobenzylamino)-5-nitro-
pyrimidin-2-ylamino)propylcarbamate (12)

A 100 mL round-bottom flask under argon atmosphere was charged with 12 [700 mg, 2.08 mmol] and DMSO [8 mL, anh.] at RT. A DMSO [5 mL, anh.] solution of N-(3-Aminopropyl)carbamic acid tert-butyl ester [362 mg, 2.08 mmol] and N,N-Diisopropylethylamine [543 μL, 3.12 mmol] was added dropwise over 3 minutes. The mixture stirred for 1 h and the volatiles were then removed in vacuo. The residue was taken up in Ethyl acetate [30 mL] and washed with sat. aq. NaCl [5×20 mL] to give crude 12 [quantitative yield] which was used in the subsequent reduction step without further manipulation.

tert-Butyl-3-(4-(2,6-dichlorobenzylamino)-5-ami-
nopyrimidin-2-ylamino)propylcarbamate (13)

A 250 mL round-bottom flask equipped with a two-way stopcock was charged with 12 [980 mg, 2.08 mmol] and MeOH [25 mL] at RT. A suspension of Raney® 2800 Nickel in water [ca. 2-3 mL] was added. Under vigorous stirring, the flask was evacuated and subsequently filled with H$_2$ [1 atm, balloon]. After 2.5 h, the H$_2$ was removed and the suspension filtered over fluted paper with MeOH washes. The aqueous methanolic filtrate was concentrated by rotoevaporation to a residue and dried diligently in vacuo to give crude 13 [1.38 g, 100%+yield] as a tan foam/oil, used in the subsequent acylation/cyclization step without further manipulation.

tert-Butyl-3-(9-(2,6-dichlorobenzyl)-8-oxo-8,9-dihy-
dro-7H-purin-2-ylamino)propylcarbamate (14)

A 250 mL round-bottom flask under argon was charged with 13 [730 mg corrected, 1.66 mmol corrected] and THF [18 mL, anh] at RT. Solid 1,1'-Carbonyldiimidazole [806 mg, 4.97 mmol] was added to the tan solution. After 75 min., the resulting orange suspension was concentrated in vacuo to a crude orange oil/solid from which 14 [302 mg] was isolated by flash chromatography using a gradient of MeOH [0-7%] in DCM.

9-(2,6-dichlorobenzyl)-2-(3-aminopropylamino)-7H-
purin-8(9H)-one (120)

A 250 mL round-bottom flask was charged with 14 [207 mg, 443 μmol] and HCl/Ethanol [14.5% wt./wt. solution, 10 mL]. The white suspension stirred at RT overnight and was then concentrated by rotoevaporation to near-dryness. The contents were then repeatedly co-evaporated with Methanol to give an off-white solid from which pure 120 was isolated by flash chromatography as the free-base [113 mg, 69% yield] using a gradient of Methanol [2-20%] in DCM with 0.5-3% aqueous NH$_3$. Treatment of the free-base [75 mg] with HCl/Ethanol [14.5% wt./wt. solution, 5 mL] for 1 hour, followed by concentration in vacuo gave pure 120 as the HCl salt [82 mg].

Data for 9-(2,6-dichlorobenzyl)-2-(3-aminopropylamino)-7H-purin-8(9H)-one (120): $^1$H NMR (300 MHz, CD$_3$OD): δ 7.85 (s, 1H), 7.59-7.52 (m, 2 H), 7.45 (dd, 1 H), 5.45 (s, 2H), 3.52 (t, 2H), 3.04 (Br t, 2H), 1.92 (quint., 2H); MS (ESI) m/z 367.0/369.0 [M+H]$^+$.

Synthesis of (S)-3-(2,6-dichlorobenzyl)-5-(pyrroli-
din-3-ylmethylamino)-1H-imidazo[4,5-b]pyridin-2
(3H)-one (Compound 147)

One possible process for (R)-3-(2,6-dichlorobenzyl)-5-(pyrrolidin-3-ylmethylamino)-1H-imidazo[4,5-b]pyridin-2(3H)-one (147) is demonstrated in Scheme 5 below and detailed in the following description.

Scheme 5.

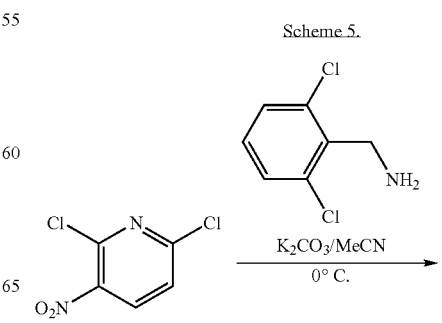

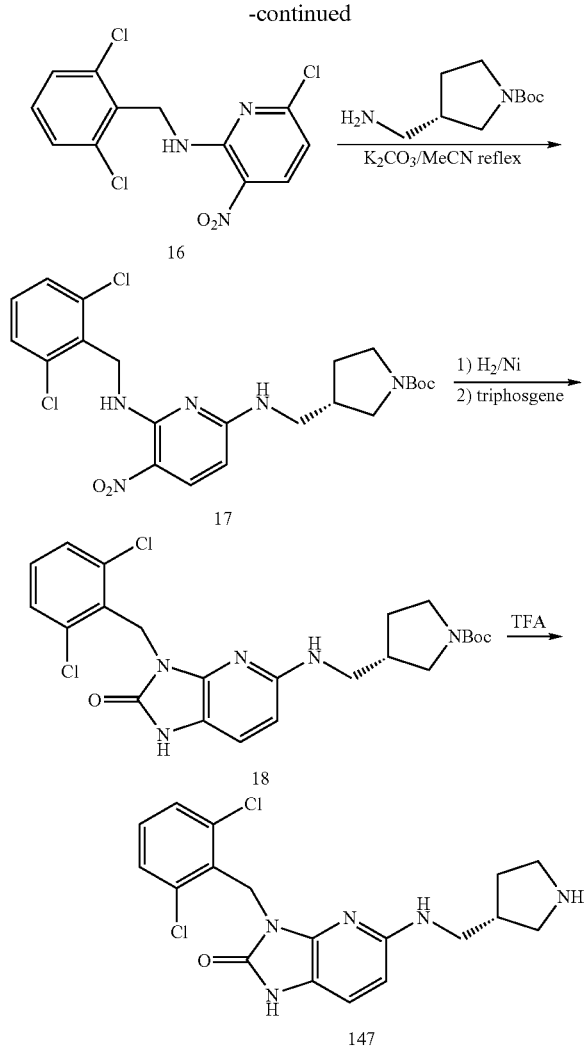

N-(2,6-Dichlorobenzyl)-6-chloro-3-nitropyridin-2-amine (16)

To a mixture of 2,6-dichloro-3-nitropyridine (1.0 g, 5.18 mmol) and potassium carbonate (848 mg, 6.14 mmol) in 15 mL MeCN was added 2,6-dichlorobenzylamine (0.63 mL, 5.18 mmol) at 0° C. The reaction mixture was stirred for one hour at 0° C. and then for 10 hours at room temperature. The organic solvent was evaporated and the residue was purified by silica gel chromatography (EtOAc:Hex=1:10) giving 16 [511 mg].

Data for N-(2,6-Dichlorobenzyl)-6-chloro-3-nitropyridin-2-amine (16): MS (ESI) m/z 331/333 [M+H]$^+$.

(S)-tert-Butyl 3-((6-(2,6-dichlorobenzylamino)-5-nitropyridin-2-ylamino)methyl)pyrrolidine-1-carboxylate (17)

A mixture of 16 (100 mg, 0.34 mmol), (S)-tert-Butyl-3-(aminomethyl)pyrrolidine-1-carboxylate (0.4 g, 2.0 mmol), potassium carbonate (56.4 mg, 0.41 mmol) in 10 mL MeCN was stirred at reflux for 2 hours. The solvent was removed by vacuum and the residue was purified by silica gel chromatography (MeOH:DCM=1:10) giving 17 [46 mg, 27% yield].

Data for (S)-tert-butyl 3-((6-(2,6-dichlorobenzylamino)-5-nitropyridin-2-ylamino)methyl)pyrrolidine-1-carboxylate (17): MS (ESI) m/z 495/497 [M+H]$^+$.

(S)-tert-Butyl 3-((3-(2,6-dichlorobenzyl)-2-oxo-2,3-dihydro-1H-imidazo[4,5-b]pyridin-5-ylamino)methyl)pyrrolidine-1-carboxylate (18)

Under an argon atmosphere, a suspension of Raney® 2800 Nickel in water [3 mL] was carefully rinsed with THF (anh., 8 X sip-and-spit) to remove the bulk of the H$_2$O. THF [5 mL, anh.] was added to this washed Raney Nickel, followed by intermediate 6 (15 mg, 0.03 mmol). The flask was filled with H$_2$ [1 atm, balloon] and the suspension was stirred vigorously for 4 hours. A THF [2 mL, anh.] solution of triphosgene [3.8 mg] was then added to the crude aniline-containing reaction mixture. After 1 h, the solvent was removed in vacuo and the crude residue was applied to a preparative TLC plate (MeOH:DCM=1:10) from which pure 18 was isolated [8.9 mg, 60% yield over 2 steps].

Data for (S)-tert-butyl 3-((3-(2,6-dichlorobenzyl)-2-oxo-2,3-dihydro-1H-imidazo[4,5-b]pyridin-5-ylamino)methyl)pyrrolidine-1-carboxylate (18): MS (ESI) m/z 491/493 [M+H]$^+$.

(R)-3-(2,6-Dichlorobenzyl)-5-(pyrrolidin-3-ylmethylamino)-1H-imidazo[4,5-b]pyridin-2(3H)-one (147)

Intermediate 18 [8.9 mg, 18 µmol] was treated with TFA-DCM [1:1, 3 mL] for 2 hours at RT. The solvent was removed in vacuo and the residue applied to a preparative RP—HPLC column from which pure 147 [6.3 mg, 69% yield] was isolated as the TFA salt.

Data for (R)-3-(2,6-dichlorobenzyl)-5-(pyrrolidin-3-ylmethylamino)-1H-imidazo[4,5-b]pyridin-2(3H)-one (147): $^1$H NMR (300 MHz, CD$_3$OD): δ 7.62 (d, 2H), 7.50 (dd, 1H), 7.28 (d, 1H), 6.35 (d, 1H), 5.53 (s, 2H), 3.35-3.55 (m, 9H), 3.15 (m, 1H), 2.75 (m, 1H), 2.33 (m, 1H), 1.90 (m, 1H); MS (ESI) m/z 392.0/394.0 [M+H]$^+$.

Solid Phase Synthesis of Purinone Analogs

One possible process for solid phase synthesis of purinone analogs of the invention is demonstrated in Scheme 6 below and detailed in the following description.

Scheme 6.

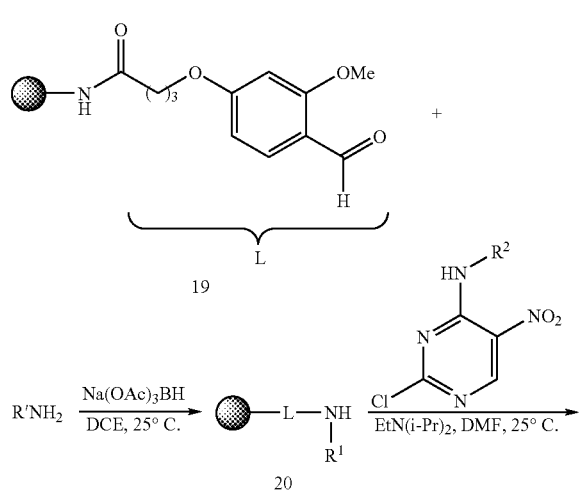

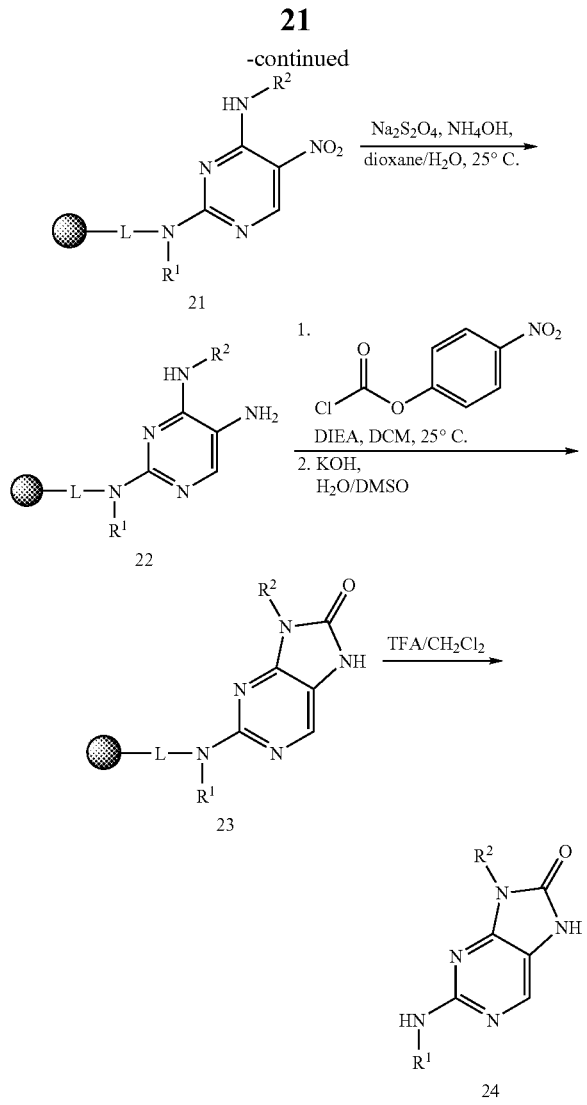

Step 1: Reductive Amination with a Primary Amine

To a 100 mL shaking vessel containing a suspension of 3.8 g (~0.8 mmol/g, 3.0 mmol, 1.0 eq.) of resin-bound o-methoxybenzaldehyde 19 in 30 mL of 1,2-dichloroethane (DCE) was added 24 mmol (0.40 M, 8.0 eq.) of an amine (see Table 1 for the 43 amines used in the library). The resin suspension was shaken for 15 sec and 5.1 g (24 mmol, 0.40 M, 8.0 eq.) of sodium triacetoxyborohydride was added followed by 30 mL of 1,2-dichloroethane. The suspension was shaken for 16 h at 25° C. The shaking vessel was then drained, and the resin was washed with $CH_3OH$ (1×), $CH_2Cl_2$ (2×), $CH_3OH$ (1×), $CH_2Cl_2$ (2×), $CH_3OH$ (1×), $CH_3OH$ (1×30 min) and $CH_2Cl_2$ (2×). The resulting resin-bound secondary amine 20 gave a positive result with the bromophenol blue staining test. The resin was dried in vacuo.

Step 2: N-arylation with 4-amino-2-chloro-5-nitropyrimidine

To 5.3 g (~0.7 mmol/g, 3.7 mmol, 1.0 eq.) of resin-bound secondary amine 20 in 25 mL of DMF and 2.18 mL of N,N-diisopropylethylamine (12.5 mmol, 0.25 M, 3.4 eq.) in a 100 mL shaking vessel was added a solution of 12.5 mmol (0.25 M, 3.4 eq.) of an 4-amino-2-chloro-5-nitropyrimidine in 25 mL of DMF. The mixture was shaken at 25° C. for 16 h. The shaking vessel was drained and the resin was washed with DMF (2×), $CH_2Cl_2$ (1×), DMF (1×), $CH_2Cl_2$ (2×), $CH_3OH$ (2×) and $CH_2Cl_2$ (2×). The resulting resin-bound nitropyrimidine 21 gave a negative result with the bromophenol blue staining test. The resin was dried in vacuo.

Step 3: Reduction of the Nitro Group

To a solution of 5.22 g (30.0 mmol, 0.5 M, 45 eq.) of sodium hydrosulfite in 40 mL of $H_2O$ was added 20 mL of 1,4-dioxane followed by 1.86 mL of a saturated aqueous solution of ammonia. This solution was added to a medium shaking vessel containing 1.1 g (~0.6 mmol/g, 0.66 mmol, 1.0 eq.) of the resin-bound 5-nitropyrimidine 21. The resin suspension was shaken for 2 h at 25° C. The shaking vessel was drained and the resin was washed with $H_2O$:1,4-dioxane 2:1 (v/v) (1×). The shaking vessel was recharged with 60 mL of a freshly prepared 0.5 M solution of sodium hydrosulfite in 40 mL of $H_2O$ and 20 mL of 1,4-dioxane and 0.93 mL of a saturated aqueous solution of ammonia that was prepared as described above. The resin suspension was shaken for 16 h at 25° C. The shaking vessel was drained and the resin was washed with $H_2O$:1,4-dioxane 2:1 (v/v) (2×), anhydrous $CH_3OH$ (2×), anhydrous DMF (2×), $CH_2Cl_2$ (2×) and anhydrous THF (2×). The resulting resin-bound 5-aminopyrimidine 22 gave a positive result with the bromophenol blue staining test. The resin was dried in vacuo.

Step 4: Formation of Purinone Ring

To a suspension of 1.54 g (~0.6 mmol/g, 0.93 mmol, 1.0 eq.) of the resin-bound 5-aminopyrimidine 22 in 30 mL of $CH_2Cl_2$ and 5.23 mL (30 mmol, 0.5 M, 32.2 eq.) of N,N-diisopropylethylamine in a medium shaking vessel was added a solution of 6.0 g (30 mmol, 0.5 M, 32.2 eq.) of p-nitrophenylchloroformate in 30 mL of $CH_2Cl_2$. The resulting resin suspension was shaken for 18 h at 25° C. The shaking vessel was then drained and the resin was washed with $CH_2Cl_2$ (2×), $CH_3OH$ (2×), $CH_2Cl_2$ (2×), $CH_3OH$ (2×) and $CH_2Cl_2$ (2×). The resulting resin gave a negative result with the bromophenol blue staining test and was used without drying. To this resin was added 60 mL of a solution of 1.68 g (30 mmol, 0.5 M, 32.2 eq.) of KOH in 15 mL of $H_2O$ and 45 mL of DMSO. The resulting resin suspension was shaken for 18 h. The shaking vessel was then drained and the resin washed with $H_2O$:DMSO 1:3 (v/v), $CH_3OH$ (2×), DMF (2×), $CH_3OH$ (2×) and $CH_2Cl_2$ (2×). The resulting resin-bound purinone 23 was dried in vacuo.

Step 5: Cleavage from Resin

To the resin-bound purinone 23 (0.5 g) was added 10 mL of a 1:1 mixture of $CH_2Cl_2$/TFA (v/v). To mixture was stirred for 1 h at 25° C. The resin was removed by filtration and filtrate was evaporated to afford 24, which was purified by either flash chromatography or semi-preparative HPLC.

PKC-Theta IMAP Assay

The activity of the compounds described in the present invention may be determined by the following procedure. This procedure describes a kinase assay that measures the phosphorylation of a fluorescently-labeled peptide by full-length human recombinant active PKCθ via fluorescent polarization using commercially available IMAP reagents.

The PKCθ used was made from full-length, human cDNA (accession number LO1087) with an encoded His-6 sequence at the C-terminus. PKCθ was expressed using the baculovirus expression system. The protein was purified with Ni—NTA affinity chromatography yielding a protein with 91% purity.

The substrate for this assay is a fluorescently-labeled peptide having the sequence LHQRRGSIKQAKVHHVK (FITC)—$NH_2$. The stock solution of the peptide is 2 mM in water.

The IMAP reagents come from the IMAP Assay Bulk Kit, product #R8063 or #R8125 (Molecular Devices, Sunnyvale, Calif.). The kit materials include a 5× IMAP Binding Buffer and the IMAP Binding Reagent. The Binding Solution is prepared as a 1:400 dilution of IMAP Binding Reagent into the 1× IMAP Binding Buffer.

The substrate/ATP buffer for this assay consists of 20 mM HEPES, pH 7.4 with 5 mM MgCl$_2$, and 0.01% Tween-20. Additionally, the buffer contains 100 nM substrate, 20 μM ATP, and 2 mM DTT which are added fresh just prior to use. The kinase buffer containing the PKCθ consists of 20 mM HEPES, pH 7.4 with 0.01% Tween-20. This buffer also contains .2 ng/μL PKCθ and 2 mM DTT which are added fresh just prior to use.

The plates used are Corning 3710 (Corning Incorporated, Corning, N.Y.). These are non-treated black polystyrene, 384-well with flat-bottoms. The serial dilutions are performed Nunc V-bottom 96-well plates (Cat#442587, Nunc A/S, Roskilde, Denmark).

The assay procedure starts the preparation of stock solutions of compounds at 10 mM in 100% DMSO. The stock solutions and the control compound are serially diluted 1:3.16 a total of 11 times into DMSO (37 μL of compound into 80 μL of DMSO). After the serial dilution has been completed, a further dilution is performed by taking 4 μL compound and adding to 196 μL substrate/ATP Buffer. Then, 10 μL aliquots of the compounds are transferred to the Costar 3710 plate. The kinase reaction is initiated by the addition of 10 μL PKCθ. This reaction is allowed to incubate for 1 hour at ambient temperature. The reaction is then quenched by the addition of 60 μL of Binding Solution. The plate is incubated for an additional 30 minutes at ambient temperature. The assay is measured using an Acquest™ Ultra—HTS Assay Detection System (Molecular Devices) in fluorescence polarization mode using 485 nm excitation and 530 nm emission.

Table 1 illustrates several examples of the compounds of the invention. These compounds were synthesized using one of the suitable procedures described above. The molecular weight of the compounds was confirmed by mass spectroscopy (m/z). The compounds of Table 1 were tested using the above-described PKCθ IMAP assay.

All compounds in Table 1 below exhibited PKCθ IMAP assay IC$_{50}$ values equal or less than 10 μM. Entries in the 100 series exhibited IC$_{50}$ values less than 100 nM; entries in the 200 series exhibited IC$_{50}$ values less than 1 μM; and entries in the 300 series exhibited IC$_{50}$ values equal or less than 10 μM.

TABLE 1

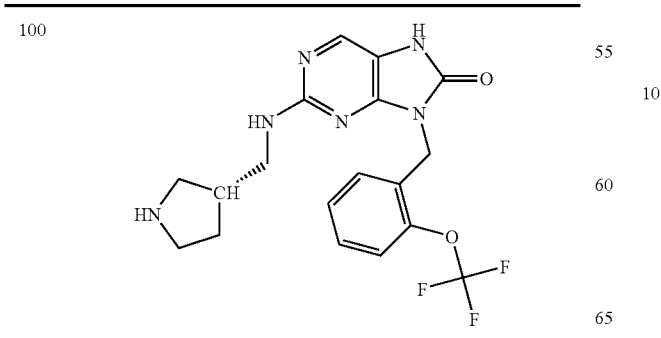

100

TABLE 1-continued

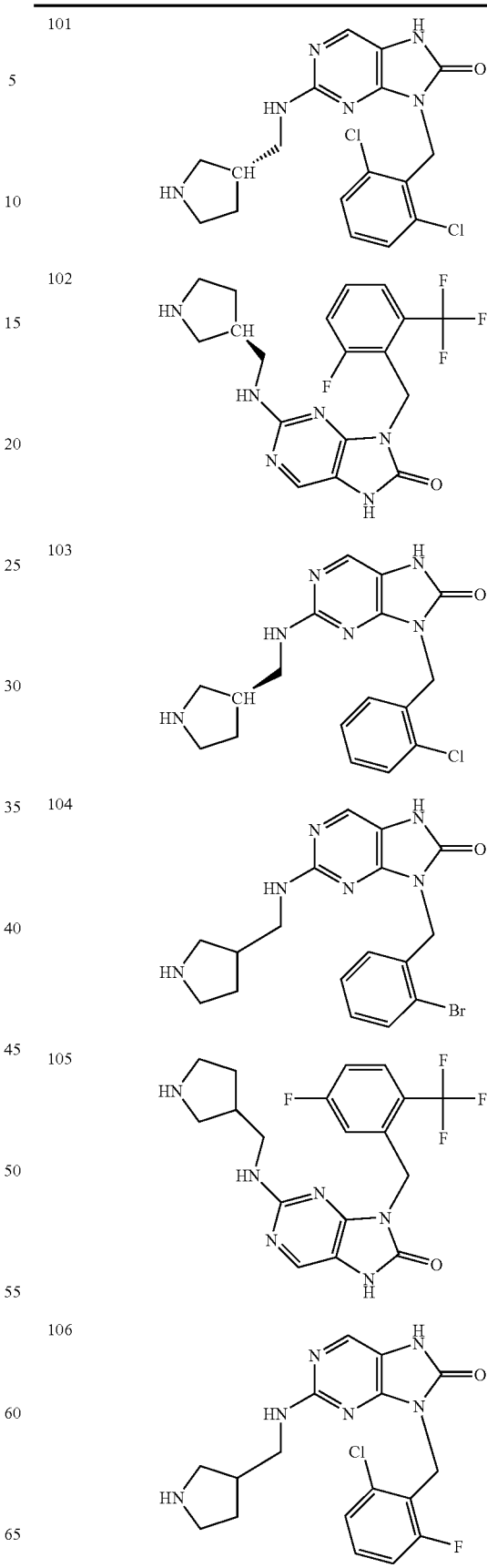

101

102

103

104

105

106

TABLE 1-continued
107 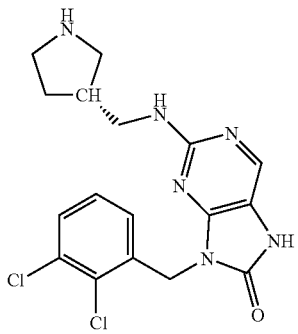
108 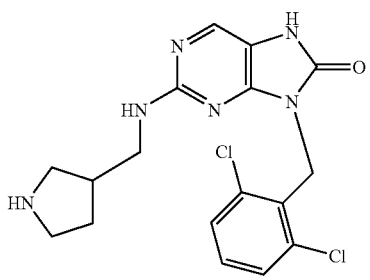
109 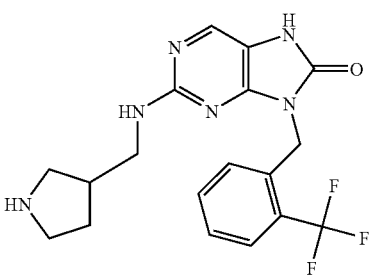
110 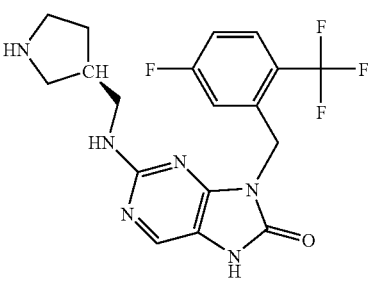
111 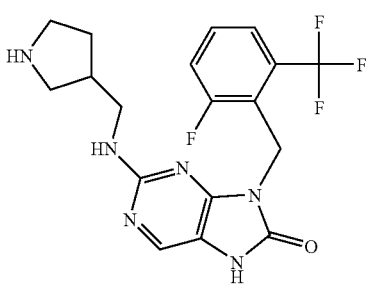
TABLE 1-continued
112 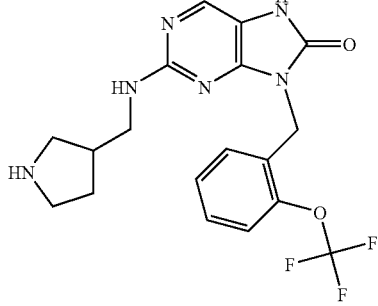
113 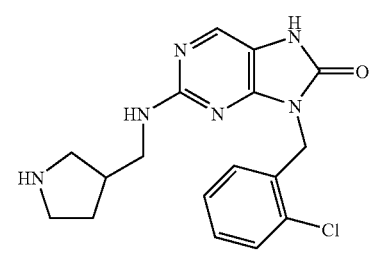
114 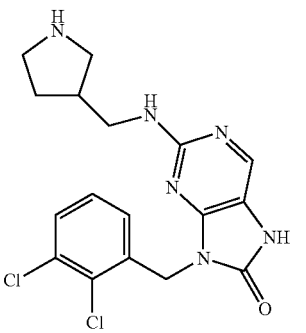
115 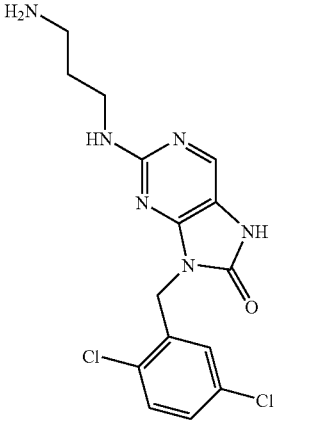
116 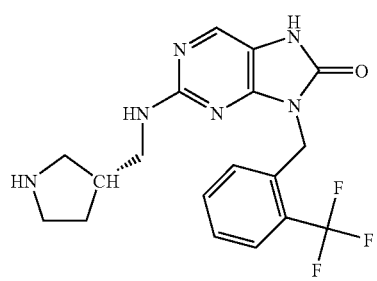

TABLE 1-continued
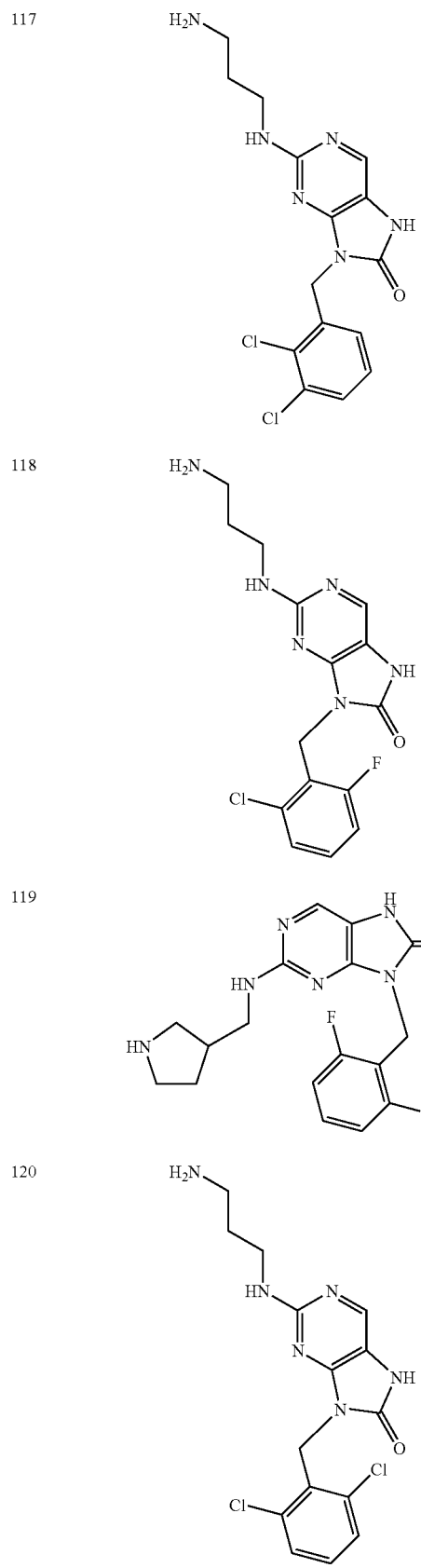
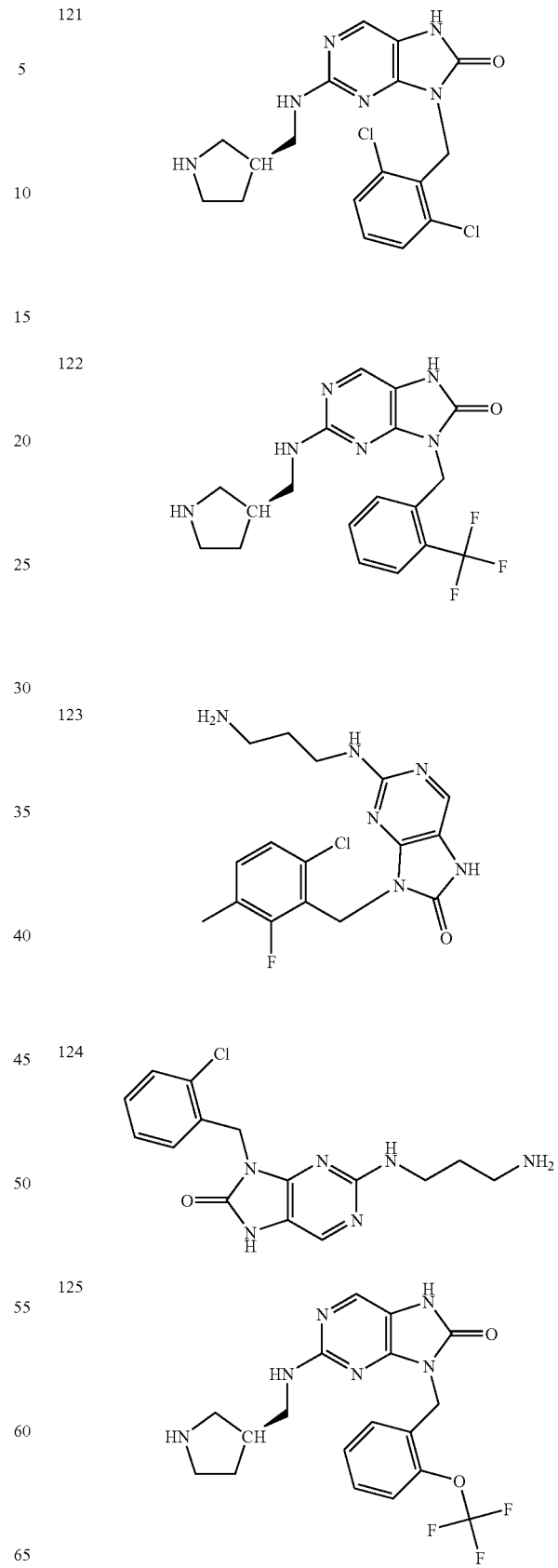

TABLE 1-continued
| 126 | 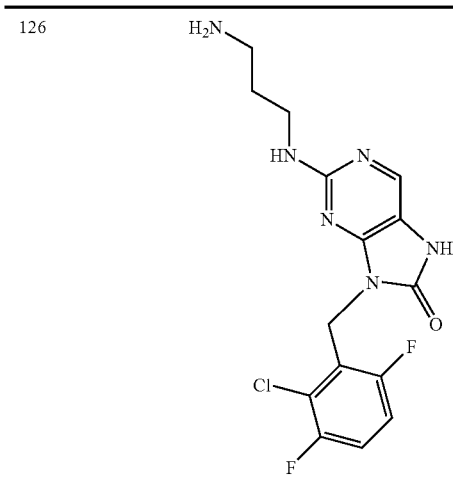 |
| --- | --- |
| 127 | 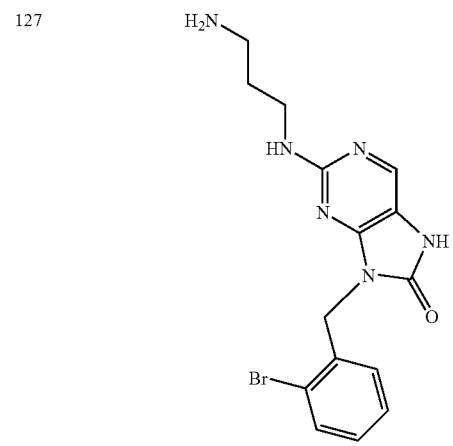 |
| 128 | 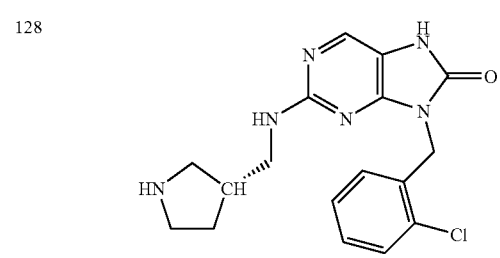 |
| 129 | 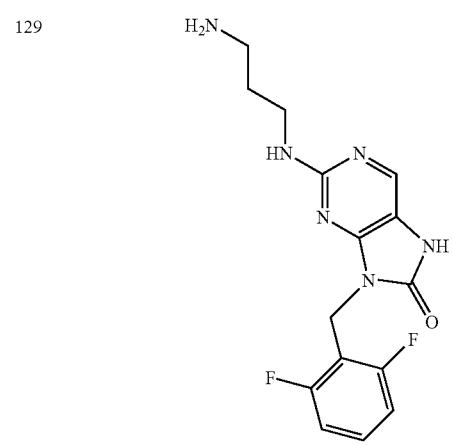 |
| 130 | 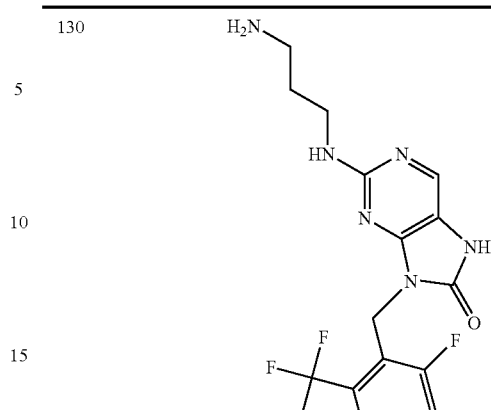 |
| 131 | 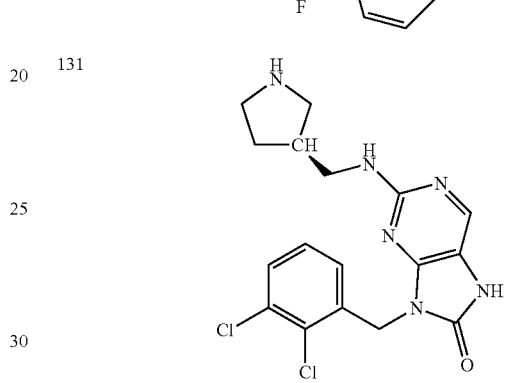 |
| 132 | 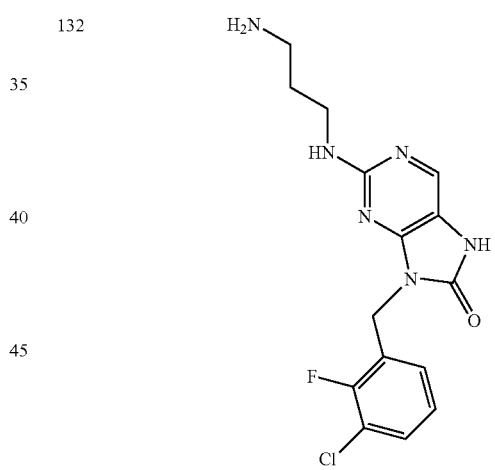 |
| 133 | 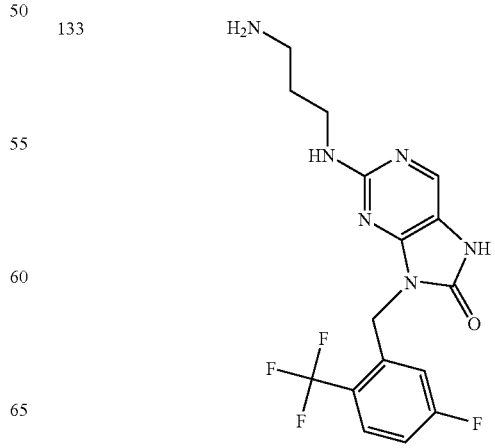 |

TABLE 1-continued
134
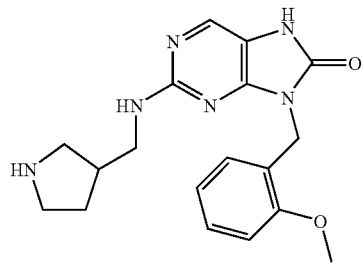
135
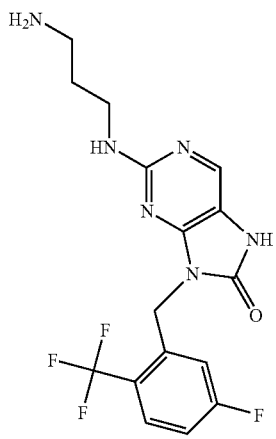
136
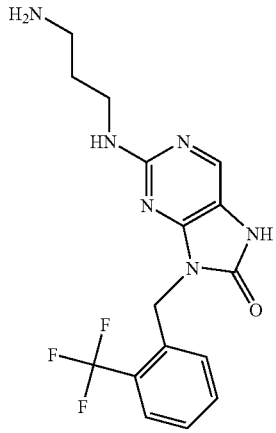
137
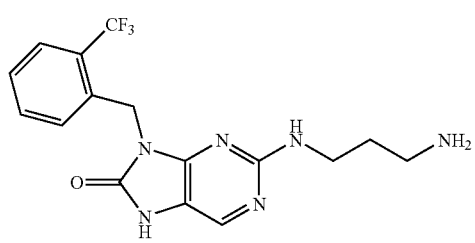
TABLE 1-continued
138
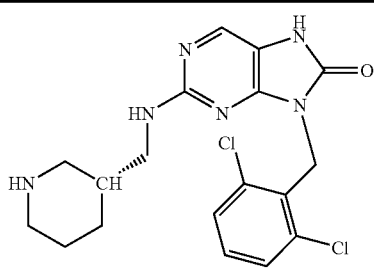
139
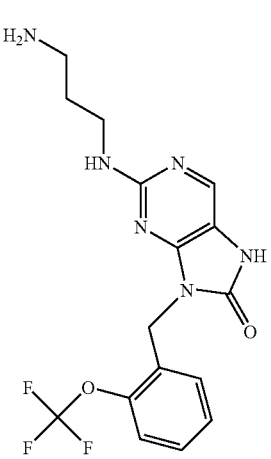
140
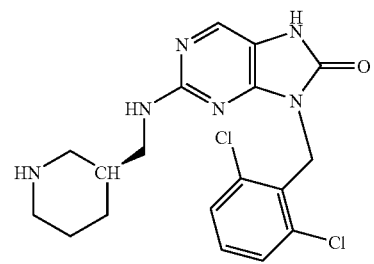
141
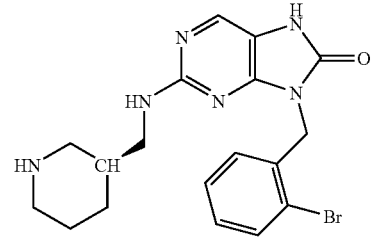
142
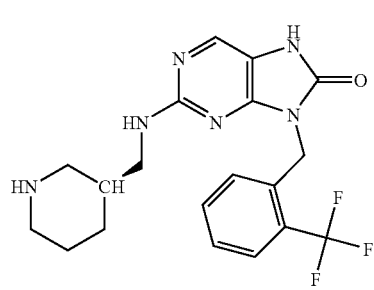

TABLE 1-continued
| 143 | 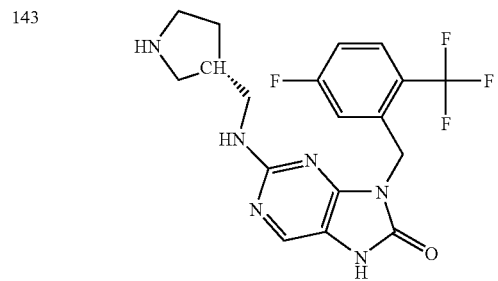 |
| --- | --- |
| 144 | 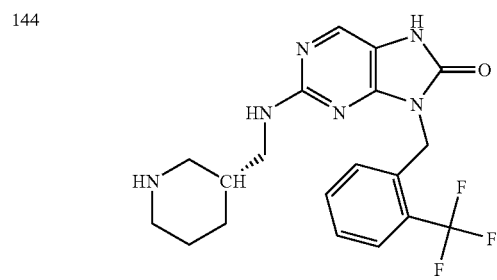 |
| 145 | 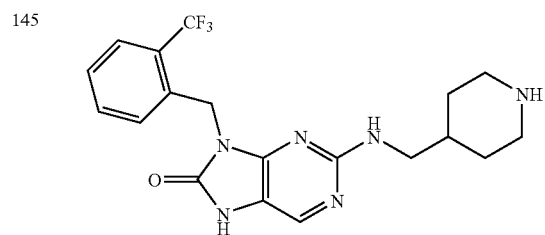 |
| 146 | 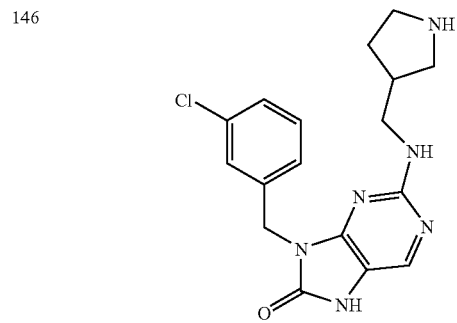 |
| 147 | 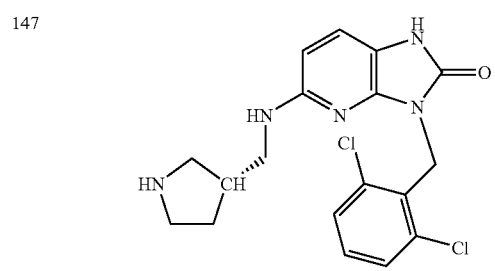 |
TABLE 1-continued
| 148 | 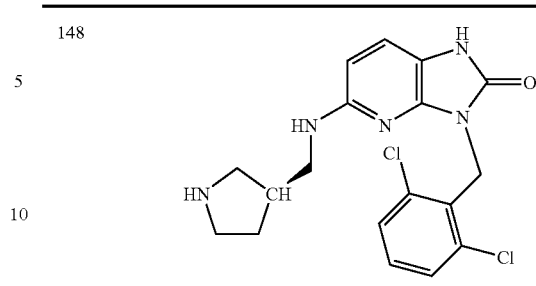 |
| --- | --- |
| 149 | 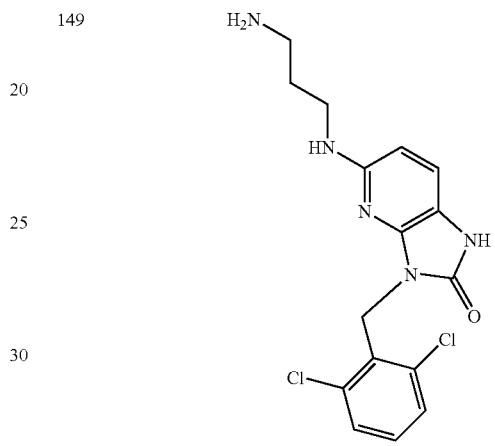 |
| 200 | 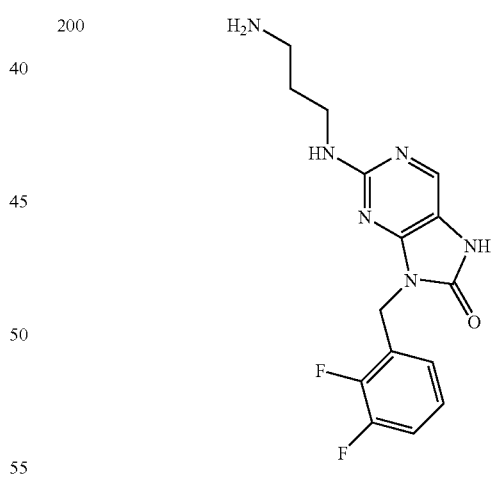 |
| 201 | 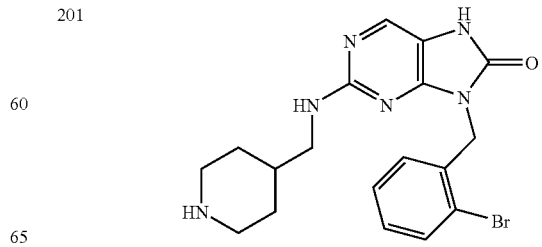 |

TABLE 1-continued
202 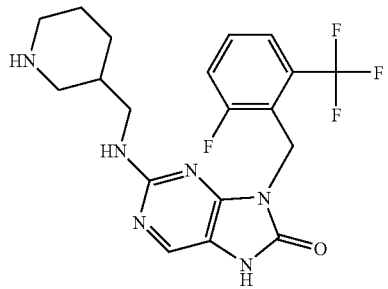
203 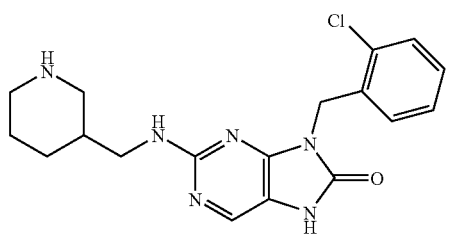
204 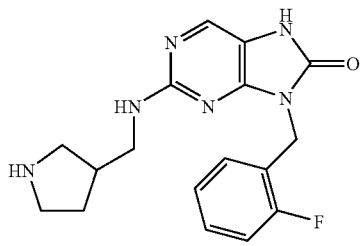
205 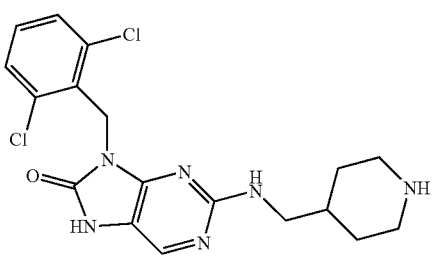
206 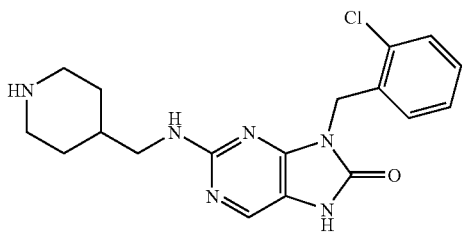
207 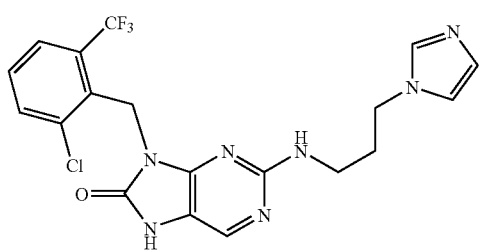
208 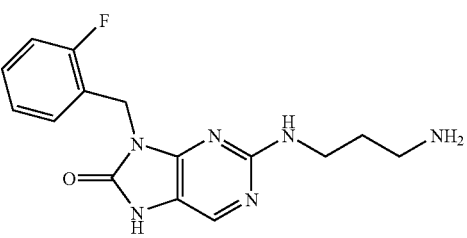
209 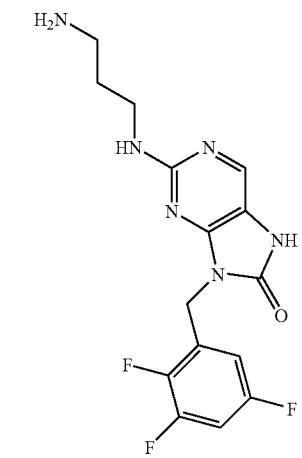
210 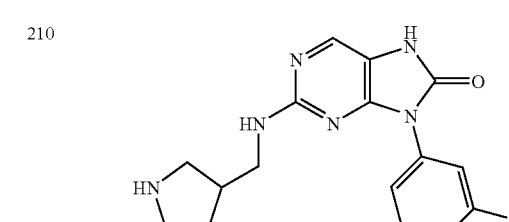
211 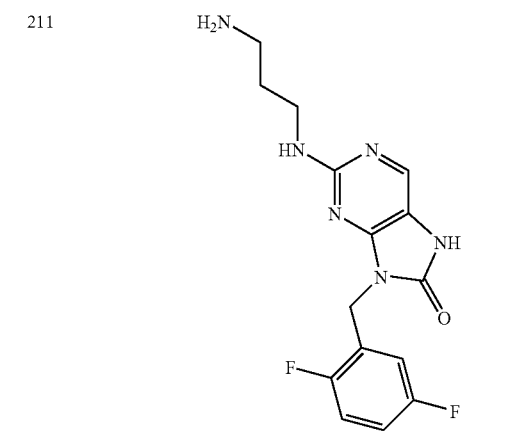

TABLE 1-continued
| 212 | 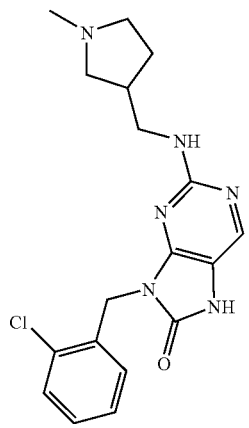 |
| --- | --- |
| 213 | 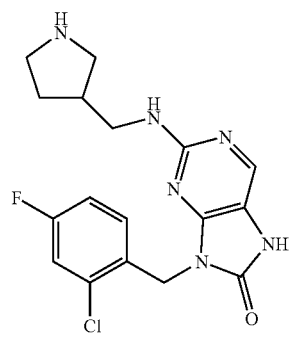 |
| 214 | 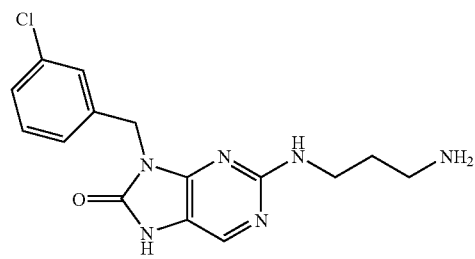 |
| 215 | 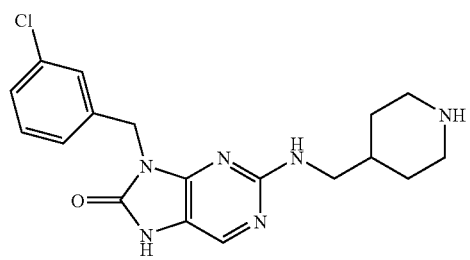 |
| 216 | 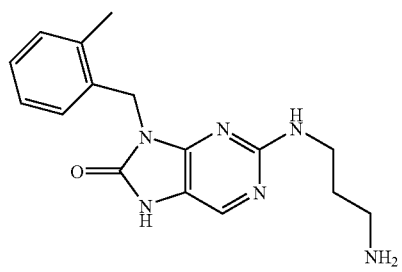 |
TABLE 1-continued
| 217 | 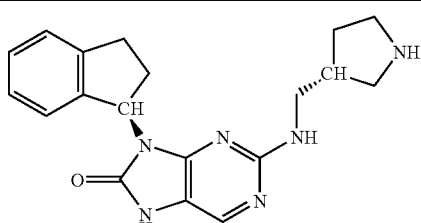 |
| --- | --- |
| 218 | 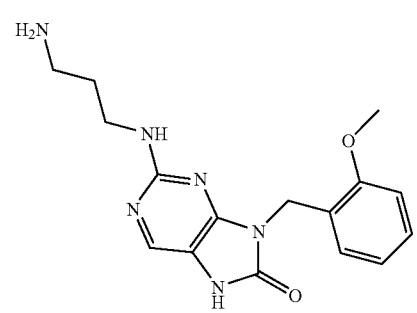 |
| 219 | 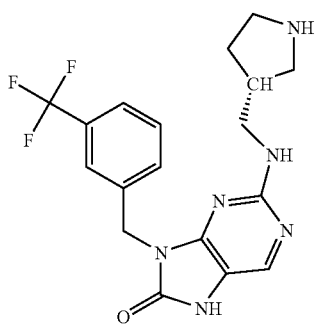 |
| 220 | 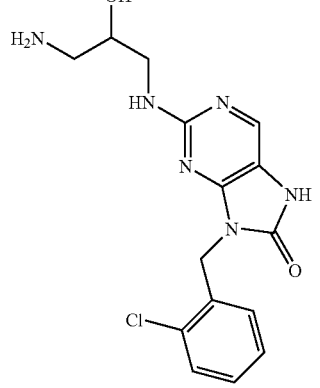 |
| 221 | 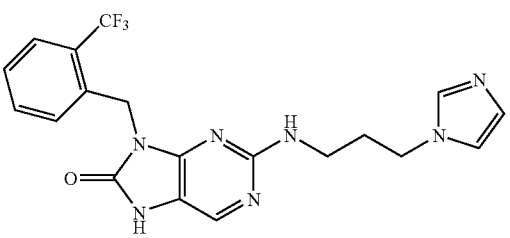 |

TABLE 1-continued
| 222 | 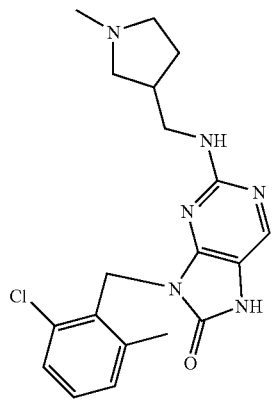 |
| --- | --- |
| 223 | 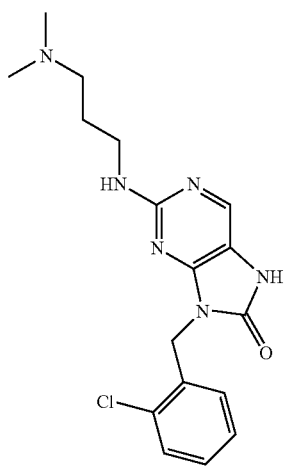 |
| 224 | 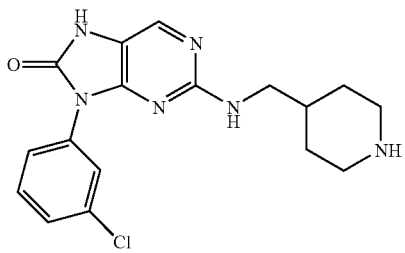 |
| 225 | 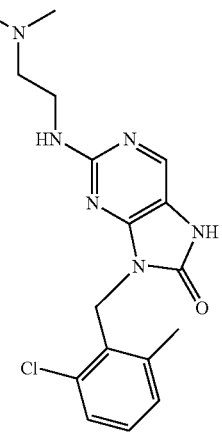 |
| 226 | 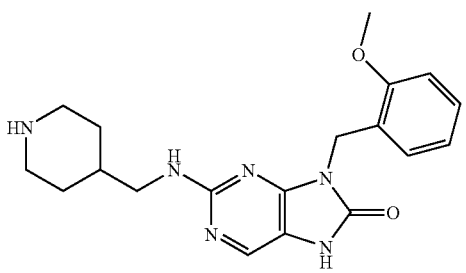 |
| 227 | 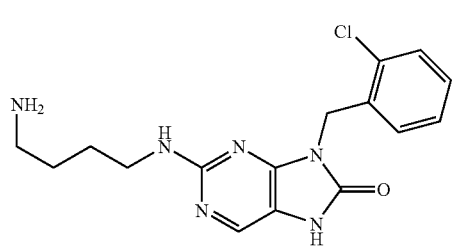 |
| 228 | 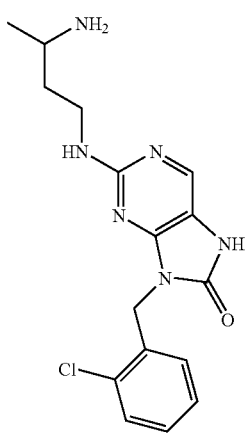 |
| 229 | 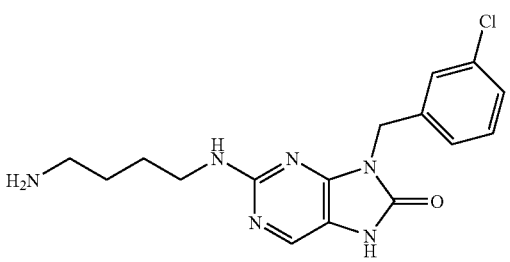 |
| 230 | 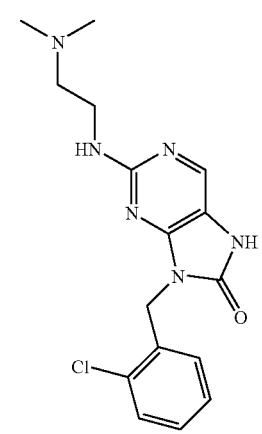 |

TABLE 1-continued
| | |
|---|---|
| 231 | 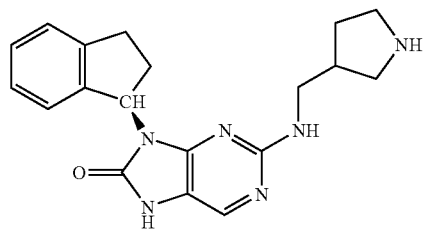 |
| 232 | 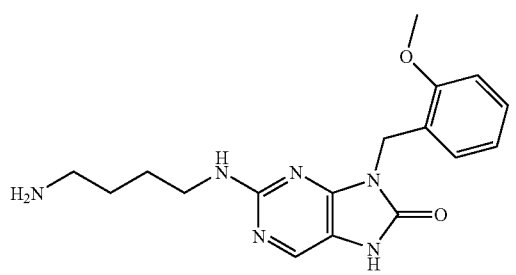 |
| 233 | 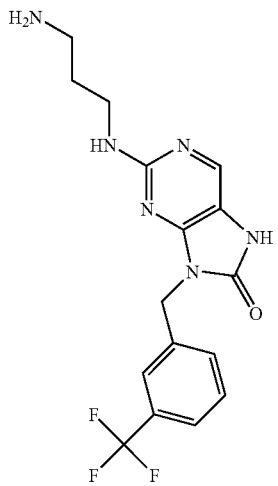 |
| 234 | 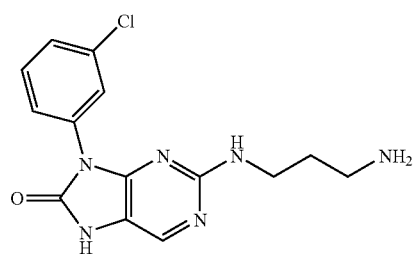 |
| 235 | 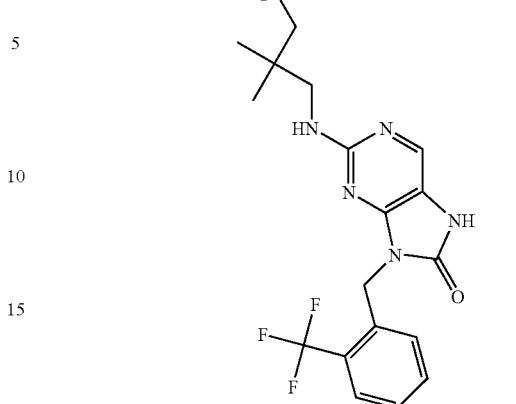 |
| 236 | 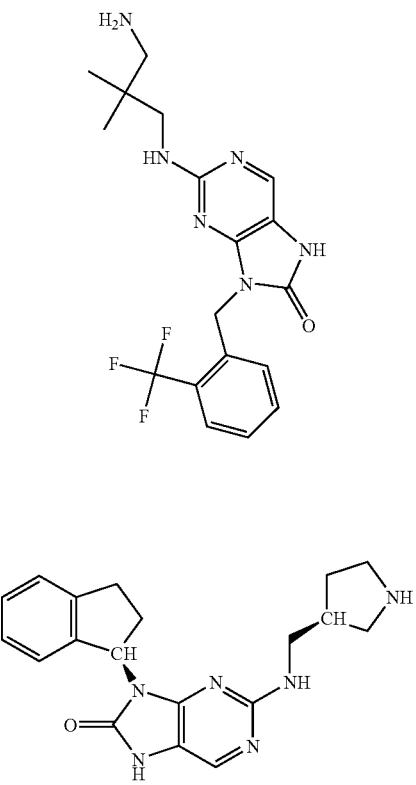 |
| 237 | 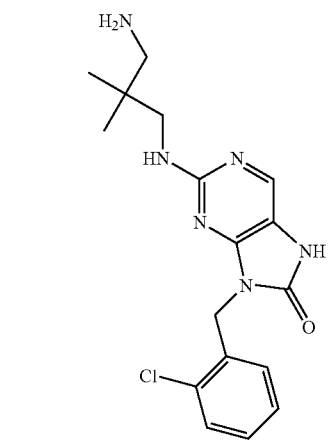 |
| 238 | 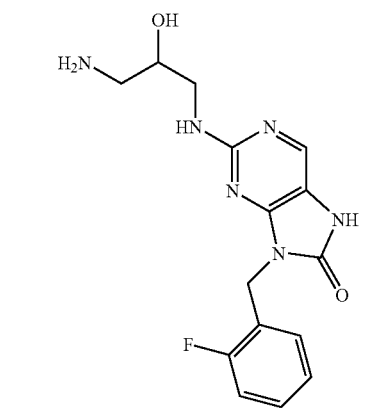 |

TABLE 1-continued
239 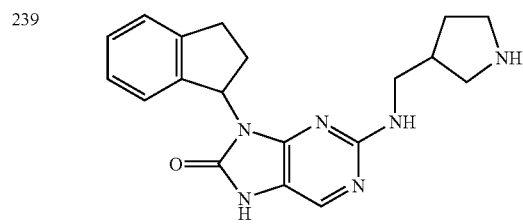
240 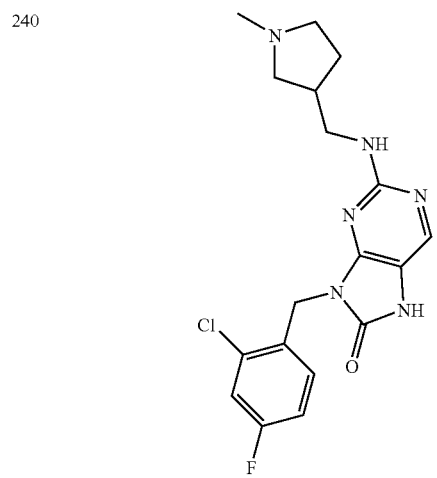
241 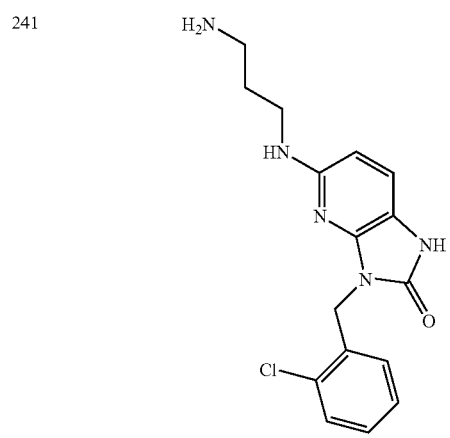
300 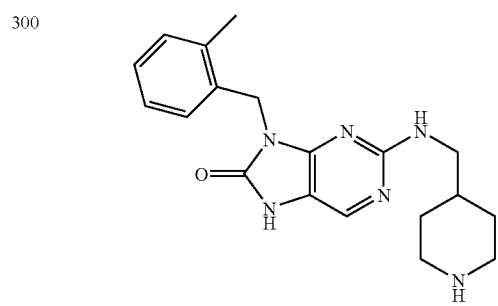
TABLE 1-continued
301 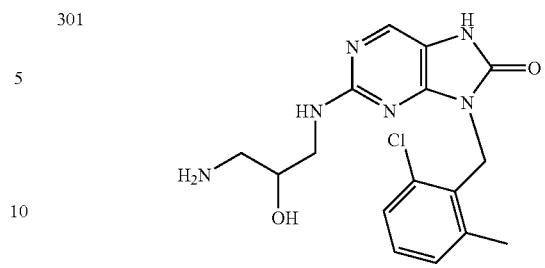
302 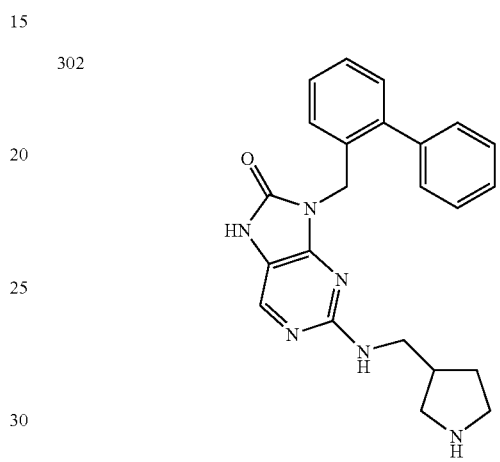
303 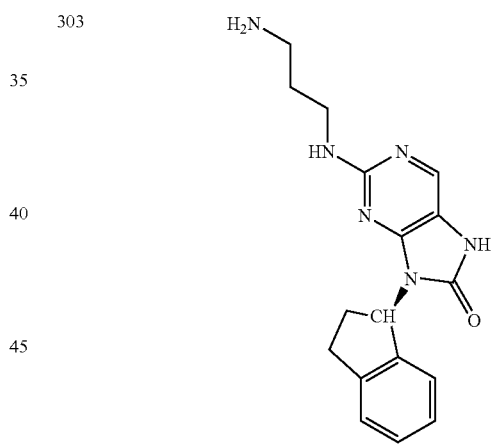
304 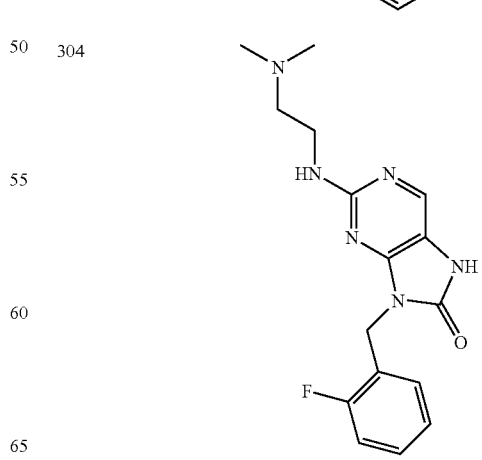

TABLE 1-continued
305 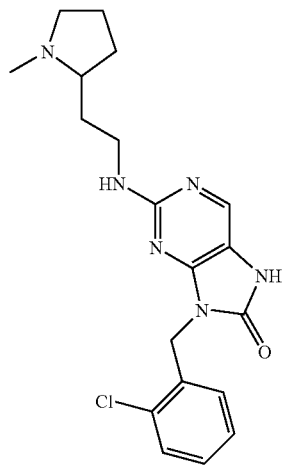
306 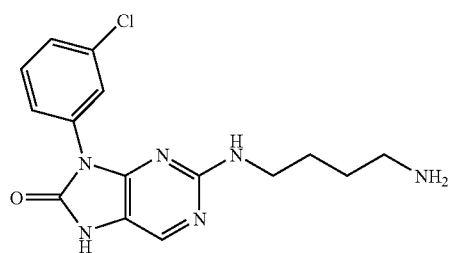
307 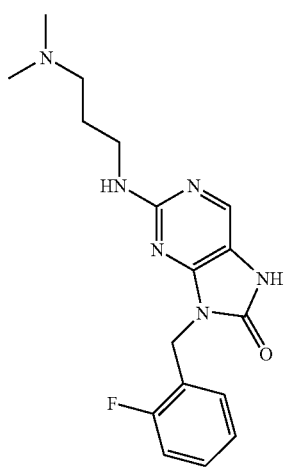
308 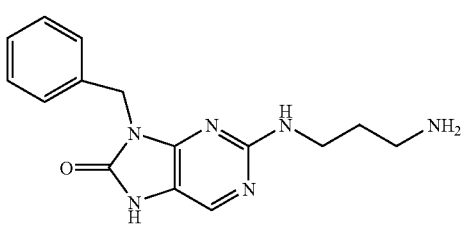
309 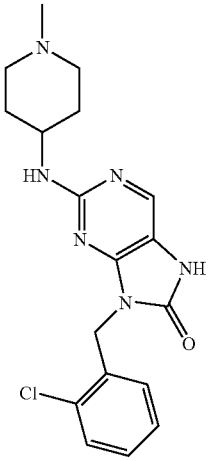
310 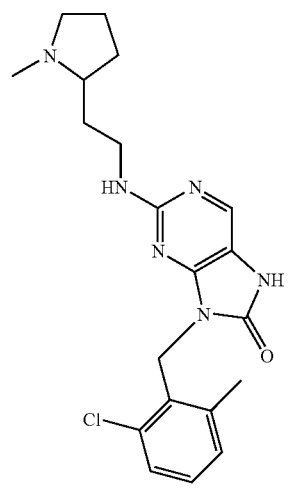
311 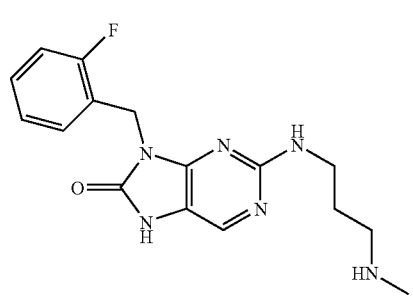

TABLE 1-continued
| 312 | 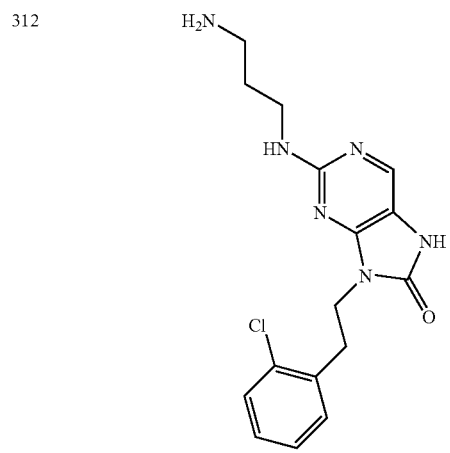 |
| 313 | 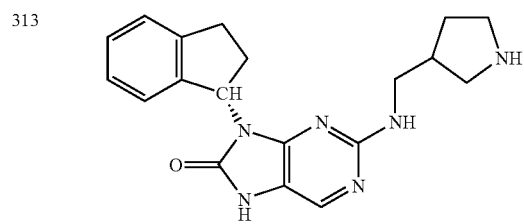 |
| 314 | 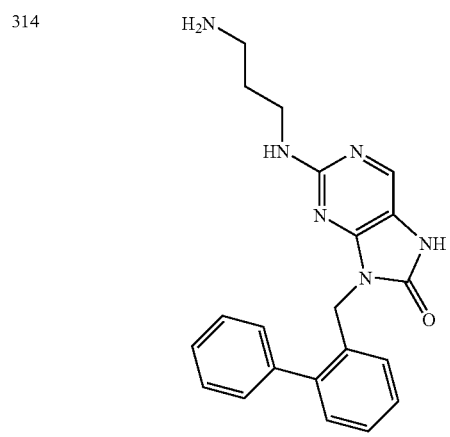 |
| 315 | 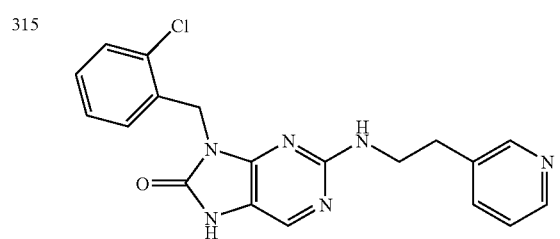 |
| 316 | 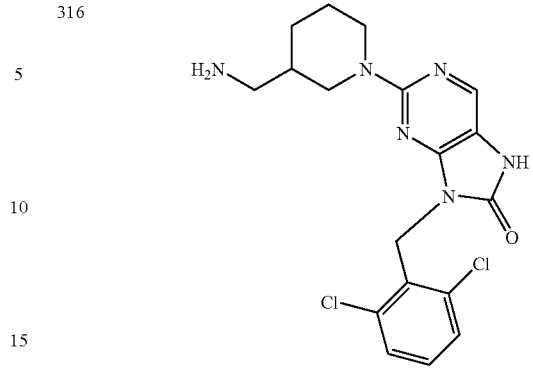 |
| 317 | 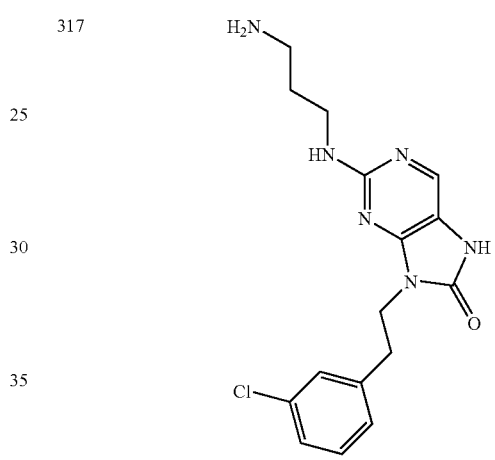 |
| 318 | 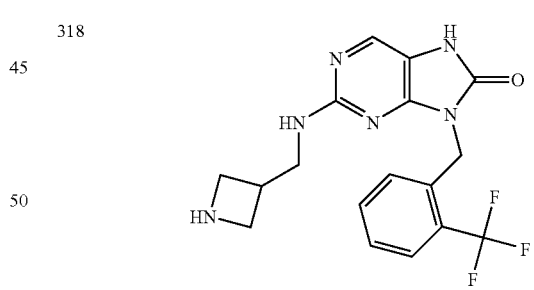 |
| 319 | 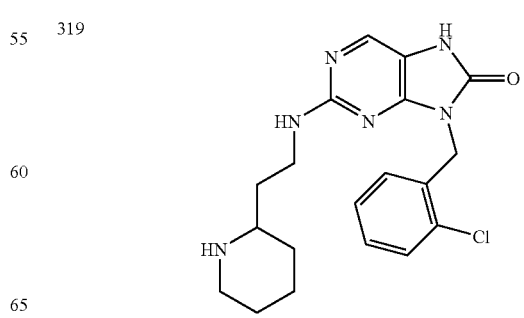 |

TABLE 1-continued
320 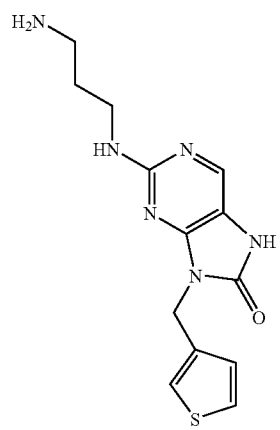
321 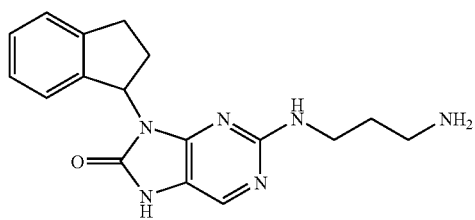
322 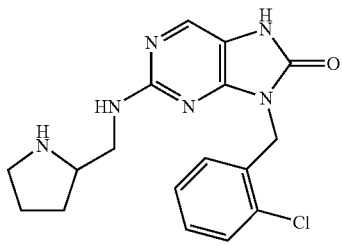
323 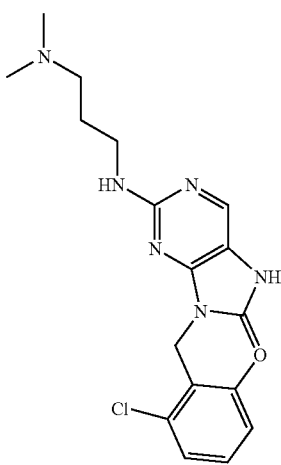
TABLE 1-continued
324 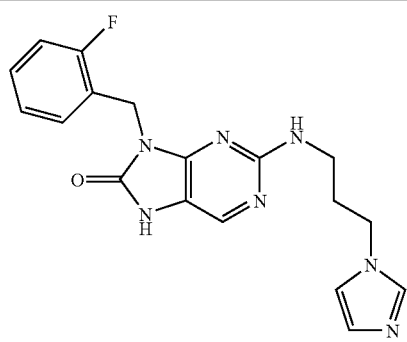
325 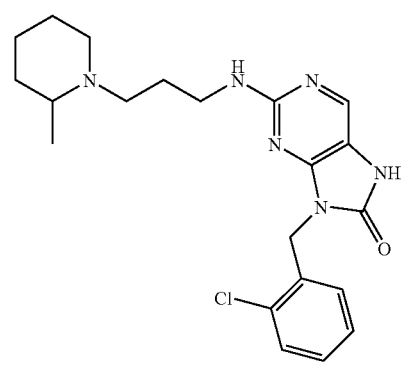
326 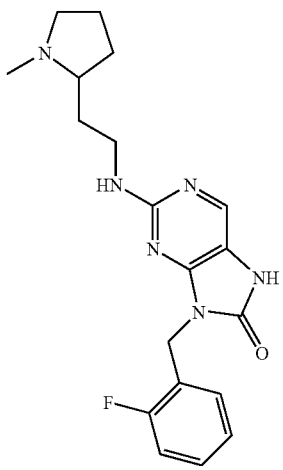
327 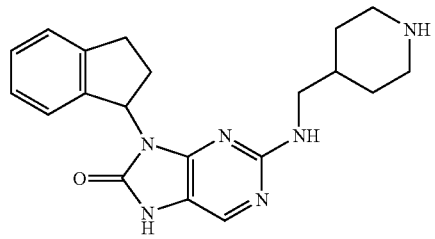

TABLE 1-continued
| | |
|---|---|
| 328 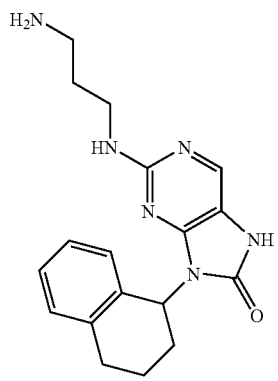 | 332 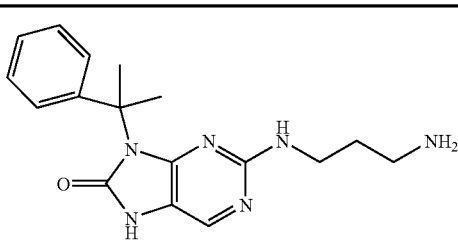 |
| 329 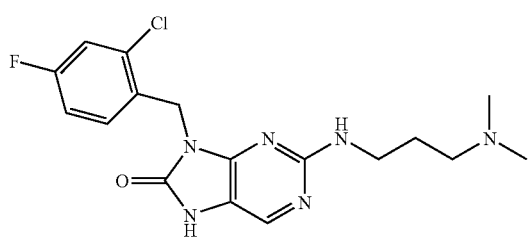 | 333 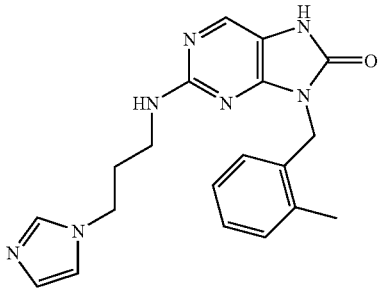 |
| 330 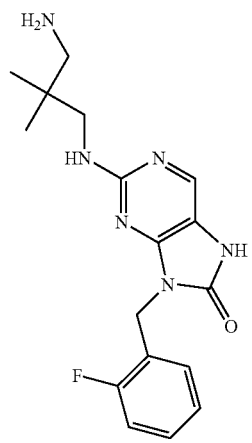 | 334 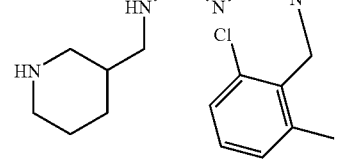 |
| 331 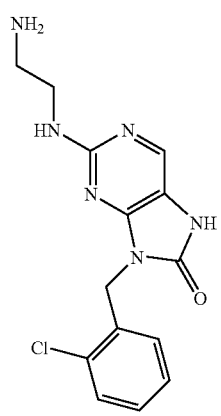 | 335 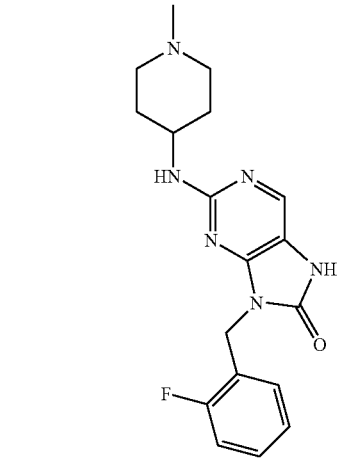 |
| | 336 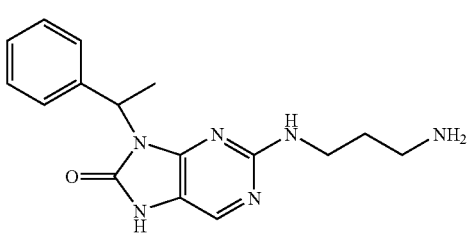 |

TABLE 1-continued

337

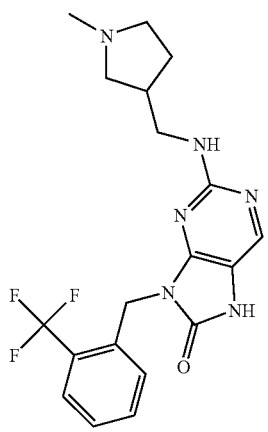

338

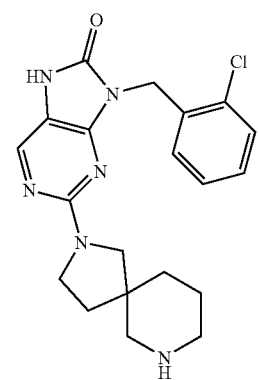

339

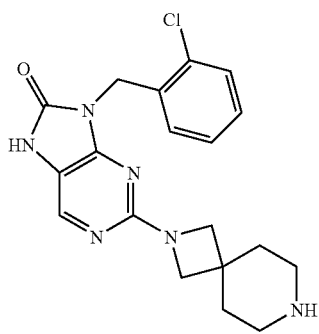

340

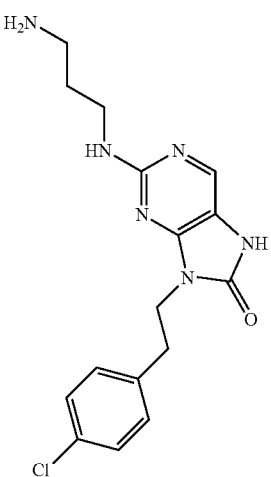

Selectivity for inhibition of PKCθ by the compounds of the invention was tested and results are shown in Table 2. The data in Table 2 shows obtained values for PKCθ isoform selectivity by showing Ki Pan Vera (PV) potencies for PKCθ, PKC delta and PKC alpha. For Ki Pan Vera (PV) of PKCθ, entries identified with "A" had values below 100 nM; entries identified with "B" had values below 1 μM. For Ki Pan Vera (PV) of PKC delta and PKC alpha, entries identified with "1" had values above 15 nM; entries identified with "2" had values above 100 nM; entries identified with "3" had values above 1 μM; entries identified with "4" had values above 10 μM.

Table 2 also shows selectivity of the compounds of the invention by showing their IC50 values for kinase SGK. Entries identified with "1" had values above 15 nM; entries identified with "2" had values above 100 nM; entries identified with "3" had values above 1 μM; entries identified with "4" had values above 10 μM. In Table 2, "nd" stands for "not determined."

TABLE 2

| Compound | Ki PV (nM) | Ki PV-delta (nM) | Ki PV-alpha (nM) | IC50-SGK1 (nM) |
|---|---|---|---|---|
| 101 | A | 1 | 3 | nd |
| 103 | A | 1 | 3 | 3 |
| 104 | A | 1 | 3 | 4 |
| 105 | A | 1 | 3 | 3 |
| 106 | A | 1 | 3 | 4 |
| 107 | A | 1 | 3 | nd |
| 108 | A | 1 | 3 | 4 |
| 109 | A | 1 | 3 | nd |
| 112 | A | 2 | 3 | Inactive |
| 113 | A | 1 | 3 | 4 |
| 114 | A | 2 | 4 | 4 |
| 115 | A | 2 | 3 | nd |
| 116 | A | 2 | 3 | 4 |
| 117 | A | 2 | 4 | Inactive |
| 118 | A | 2 | 4 | Inactive |
| 120 | A | 2 | 4 | Inactive |
| 119 | A | 2 | 4 | Inactive |
| 122 | A | 2 | 3 | Inactive |
| 124 | A | 2 | 4 | 4 |
| 127 | A | 2 | 4 | 3 |
| 128 | B | 2 | 4 | 4 |
| 129 | A | 2 | 4 | Inactive |
| 133 | A | 2 | 4 | 3 |
| 135 | A | 2 | 4 | nd |
| 136 | A | 2 | 4 | Inactive |
| 137 | A | 2 | 4 | Inactive |
| 138 | A | 2 | 4 | 4 |
| 139 | B | 3 | 4 | Inactive |
| 140 | B | 2 | 4 | 4 |
| 141 | B | 2 | 4 | Inactive |
| 142 | B | 2 | 4 | 4 |
| 144 | B | 2 | 4 | 4 |
| 145 | B | 3 | 4 | Inactive |
| 147 | A | 1 | 3 | 4 |
| 148 | A | 2 | 4 | nd |
| 149 | A | 2 | 4 | Inactive |
| 201 | B | 2 | 3 | 4 |
| 203 | B | 2 | 4 | Inactive |
| 204 | B | 2 | 4 | 4 |
| 205 | B | 2 | 4 | Inactive |
| 206 | B | 2 | 4 | Inactive |
| 207 | B | 2 | 4 | nd |
| 208 | B | 2 | 4 | Inactive |
| 214 | B | 3 | 4 | nd |
| 215 | B | 3 | 4 | nd |
| 216 | B | 3 | 4 | nd |
| 218 | B | 3 | 4 | nd |
| 224 | B | 3 | 3 | nd |
| 231 | B | 3 | 4 | nd |
| 241 | B | 2 | 4 | Inactive |

The compounds of the invention were also tested in vivo. Table 3 below demonstrates results of anti-CD3 induced interleukin-2 (IL-2) production in mice, which was performed following protocols disclosed in Goldberg et al. (2003), J. Med. Chem. 46, 1337-1349.

TABLE 3

| Compound | Subcutaneous dose mg/kg | % inhibition of IL-2 production |
| --- | --- | --- |
| Vehicle (no drug) | 0 | 0 |
| FK506 (positive control, global immunosuppression) | 1 | 87 |
| 120 | 30 | 40 |
| 101 | 30 | 39 |
| 107 | 30 | 45 |
| 115 | 30 | 40 |

IL-2 is a T cell-derived lymphokine that modulates immunological effects on many cells of the immune system, including cytotoxic T cells, natural killer cells, activated B cells and lymphokine-activated cells. It is a potent T cell mitogen that is required for the T cell proliferation, promoting their progression from G1 to S phase of the cell cycle. It is a growth factor for all subpopulations of T lymphocytes, as well as stimulating the growth of NK cells. It also acts as a growth factor to B cells and stimulates antibody synthesis.

Due to its effects on both T and B cells, IL-2 is a major central regulator of immune responses. It plays a role in anti-inflammatory reactions, tumor surveillance, and hematopoiesis. It also affects the production of other cytokines, inducing IL-1, TNF-α and TNF-β secretion, as well as stimulating the synthesis of IFN-γ in peripheral leukocytes. IL-2, although useful in the immune response, also causes a variety of problems. IL-2 damages the blood-brain barrier and the endothelium of brain vessels. These effects may be the underlying causes of neuropsychiatric side effects observed under IL-2 therapy, e.g. fatigue, disorientation and depression. It also alters the electrophysiological behavior of neurons.

T cells that are unable to produce IL-2 become inactive (anergic). This renders them potentially inert to any antigenic stimulation they might receive in the future. As a result, agents which inhibit IL-2 production may be used for immunosupression or to treat or prevent inflammation and immune disorders. This approach has been clinically validated with immunosuppressive drugs such as cyclosporin, FK506, and RS61443.

The data presented in Tables 1-3 demonstrates utility of the compounds of the invention in inhibition of PKCθ and their utility for treatment of T-cell mediated diseases including autoimmune diseases such as rheumatoid arthritis, lupus erythematosus, and multiple sclerosis, inflammatory diseases such as asthma and inflammatory bowel disease, transplant rejection, gastrointestinal cancer, and diabetes.

Some of the compounds described herein contain one or more asymmetric centers and may thus give rise to enantiomers, diastereomers, and other stereoisometric forms which may be defined in terms of absolute stereochemistry as (R)— or (S)—. The present invention is meant to include all such possible diastereomers as well as their racemic and optically pure forms. Optically active (R)— and (S)-isomers may be prepared using homo-chiral synthons or homo-chiral reagents, or optically resolved using conventional techniques. When the compounds described herein contain olefinic double bonds or other centers of geometric asymmetry, and unless specified otherwise, it is intended to include both (E)- and (Z)-geometric isomers. Likewise, all tautomeric forms are intended to be included.

The present invention includes compounds of formula (I) in the form of salts. Suitable salts include those formed with both organic and inorganic acids. Such salts will normally be pharmaceutically acceptable, although non-pharmaceutically acceptable salts may be of utility in the preparation and purification of the compound in question. The term "pharmaceutically acceptable salt" refers to salts prepared from pharmaceutically acceptable non-toxic acids or bases including inorganic acids and bases and organic acids and bases. When the compounds of the present invention are basic, salts may be prepared from pharmaceutically acceptable non-toxic acids including inorganic and organic acids. Suitable pharmaceutically acceptable acid addition salts for the compounds of the present invention include acetic, benzenesulfonic(besylate), benzoic, camphorsulfonic, citric, ethenesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric acid, p-toluenesulfonic, and the like. When the compounds contain an acidic side chain, suitable pharmaceutically acceptable base addition salts for the compounds of the present invention include metallic salts made from aluminum, calcium, lithium, magnesium, potassium, sodium and zinc or organic salts made from lysine, N,N'-dibenzylethylenediamine, chloroprocaine, choline, diethanolamine, ethylenediamine, meglumine(N-methylglucamine) and procaine.

While it may be possible for the compounds of formula (I) or their salts and solvates to be administered as the raw chemical, it is preferable to present them as a pharmaceutical composition. According to a further aspect, the present invention provides a pharmaceutical composition comprising a compound of formula (I) or a pharmaceutically acceptable salt or solvate thereof, together with one or more pharmaceutically carriers thereof and optionally one or more other therapeutic ingredients. The carrier(s) must be "acceptable" in the sense of being compatible with the other ingredients of the formulation and not deleterious to the recipient thereof.

The formulations include those suitable for oral, parenteral (including subcutaneous, intradermal, intramuscular, intravenous and intraarticular), rectal and topical (including dermal, buccal, sublingual and intraocular) administration. The most suitable route may depend upon the condition and disorder of the recipient. The formulations may conveniently be presented in unit dosage form and may be prepared by any of the methods well known in the art of pharmacy. All methods include the step of bringing into association a compound of formula (I) or a pharmaceutically acceptable salt or solvate thereof ("active ingredient") with the carrier which constitutes one or more accessory ingredients. In general, the formulations are prepared by uniformly and intimately bringing into association the active ingredient with liquid carriers or finely divided solid carriers or both and then, if necessary, shaping the product into the desired formulation.

Formulations of the present invention suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

A tablet may be made by compression or molding, optionally with one or more accessory ingredients. Compressed tablets may be prepared by compressing in a suitable machine the active ingredient in a free-flowing form such as a powder or granules, optionally mixed with a binder, lubricant, inert diluent, lubricating, surface active or dispersing agent. Molded tablets may be made by molding in a suitable machine a mixture of the powdered compound moistened with an inert liquid diluent. The tablets may optionally be coated or scored and may be formulated so as to provide sustained, delayed or controlled release of the active ingredient therein.

Formulations for parenteral administration include aqueous and non-aqueous sterile injection solutions which may contain anti-oxidants, buffers, bacteriostats and solutes which render the formulation isotonic with the blood of the intended recipient. Formulations for parenteral administration also include aqueous and non-aqueous sterile suspensions, which may include suspending agents and thickening agents. The formulations may be presented in unit-dose of multi-dose containers, for example sealed ampoules and vials, and may be stored in a freeze-dried (lyophilized) condition requiring only the addition of a sterile liquid carrier, for example saline, phosphate-buffered saline (PBS) or the like, immediately prior to use. Extemporaneous injection solutions and suspensions may be prepared from sterile powders, granules and tablets of the kind previously described.

Formulations for rectal administration may be presented as a suppository with the usual carriers, such as cocoa butter or polyethylene glycol.

Formulations for topical administration in the mouth, for example buccally or sublingually, include lozenges comprising the active ingredient in a flavored basis such as sucrose and acacia or tragacanth, and pastilles comprising the active ingredient in a basis such as gelatin and glycerin or sucrose and acacia.

Preferred unit dosage formulations are those containing an effective dose, or an appropriate fraction thereof, of the active ingredient.

The pharmaceutical compositions will usually include a "pharmaceutically acceptable inert carrier" and this expression is intended to include one or more inert excipients, which include starches, polyols, granulating agents, microcrystalline cellulose, diluents, lubricants, binders, disintegrating agents, and the like. If desired, tablet dosages of the disclosed compositions may be coated by standard aqueous or non-aqueous techniques. "Pharmaceutically acceptable carrier" also encompasses controlled release means. Compositions of the present invention may also optionally include other therapeutic ingredients, anti-caking agents, preservatives, sweetening agents, colorants, flavors, desiccants, plasticizers, dyes, and the like.

The compounds of formula (I) are preferably administered orally or by injection (intravenous or subcutaneous). The precise amount of compound administered to a patient will be the responsibility of the attendant physician. However, the dose employed will depend on a number of factors, including the age and sex of the patient, the precise disorder being treated, and its severity. Also, the route of administration may vary depending on the condition and its severity.

The contents of each of the references cited herein, including the contents of the references cited within the primary references, are herein incorporated by reference in their entirety.

The invention claimed is:
1. A compound, or salt thereof, represented by Formula I,

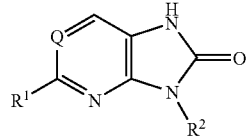

wherein:
Q is N;
$R^1$ is chosen from (i)

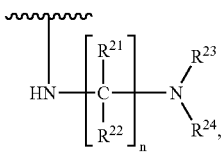

wherein
n is an integer from 2 to 6;
$R^{21}$ is chosen separately in each occurrence from —H, $C_1$-$C_4$ alkyl and —OH;
$R^{22}$ is chosen separately in each occurrence from —H, $C_1$-$C_4$ alkyl and a bond to $R^{24}$;
$R^{23}$ is chosen from —H, $C_1$-$C_4$ alkyl and a bond to $R^{24}$;
$R^{24}$ is chosen from —H, $C_1$-$C_4$ alkyl or together with either of $R^{22}$ or $R^{23}$ forms a 5-7 membered nitrogen heterocycle optionally substituted with $C_1$-$C_4$ alkyl;

(ii)

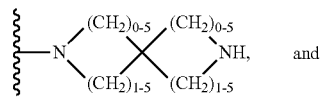

(iii)

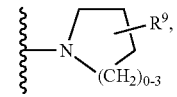

wherein $R^9$ is chosen from amino($C_1$-$C_6$)alkyl, ($C_1$-$C_6$)alkylamino($C_1$-$C_6$)alkyl and di [($C_1$-$C_6$)alkyl]amino ($C_1$-$C_6$)alkyl; and
$R^2$ is chosen from aryl, substituted aryl, arylalkyl, substituted arylalkyl, heteroaryl, substituted heteroaryl, hetroarylalkyl, and substituted heteroarylalkyl.

2. A compound, or salt thereof, according to claim 1, wherein:
$R^1$ is chosen from

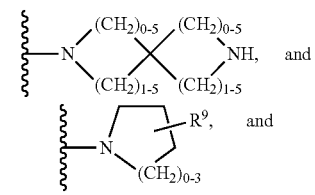

wherein $R^9$ is chosen from amino($C_1$-$C_6$)alkyl, ($C_1$-$C_6$) alkylamino($C_1$-$C_6$)alkyl and di[($C_1$-$C_6$)alkyl]amino ($C_1$-$C_6$)alkyl.

3. A compound, or salt thereof, according to claim 1, wherein:

$R^1$ is

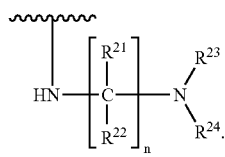

4. A compound, or salt thereof, according to claim 3, wherein:
$R^{22}$ is chosen separately in each occurrence from —H and $C_1$-$C_4$ alkyl; and
$R^{24}$ together with $R^{23}$ forms a 5-7 membered nitrogen heterocycle optionally substituted with $C_1$-$C_4$ alkyl.

5. A compound, or salt thereof, according to claim 3, wherein:
$R^{22}$ is chosen separately in each occurrence from —H and $C_1$-$C_4$ alkyl;
$R^{23}$ is chosen from —H, $C_1$-$C_4$ alkyl; and
$R^{24}$ is H or $C_1$-$C_4$ alkyl.

6. A compound, or salt thereof, according to claim 3, wherein:
$R^{22}$ is chosen separately in each occurrence from H, $C_1$-$C_4$ alkyl and a bond to $R^{24}$;
$R^{23}$ is chosen from H, $C_1$-$C_4$ alkyl;
$R^{24}$ together with one occurrence of $R^{22}$ forms a 5-7 membered nitrogen heterocycle optionally substituted with $C_1$-$C_4$ alkyl.

7. A compound, or salt thereof, according to claim 1, wherein:
$R^2$ is chosen from

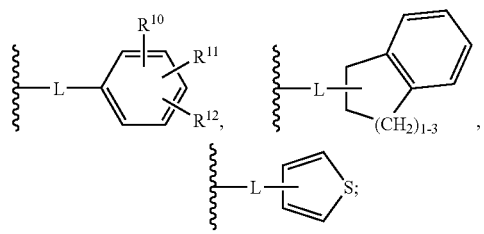

wherein
$R^{10}$, $R^{11}$, and $R^{12}$, are independently chosen from —H, halogen, —$OCH_3$, —$OCF_3$, —$CF_3$, $C_1$-$C_4$ alkyl, and phenyl; and
L is a bond or a $C_1$-$C_{10}$ alkylene.

8. A compound, or salt thereof, according to claim 7, wherein:
$R^2$ is chosen from

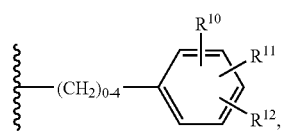

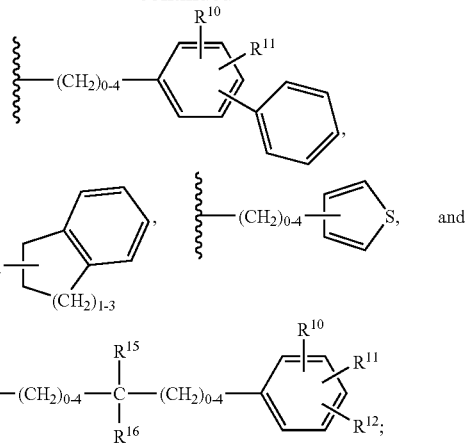

wherein
$R^{10}$, $R^{11}$, and $R^{12}$ are independently chosen from —H, halogen, —$OCH_3$, —$OCF_3$, —$CF_3$, and $C_1$-$C_4$ alkyl; and
$R_{15}$ and $R_{16}$ are independently chosen from —H and $C_1$-$C_4$ alkyl.

9. A pharmaceutical composition comprising a compound according to claim 1, or salt thereof, and a pharmaceutically acceptable carrier.

10. A compound, or salt thereof, represented by Formula I,

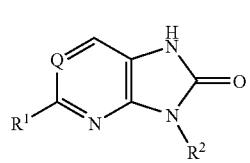

wherein:
Q is N;
$R^1$ is chosen from

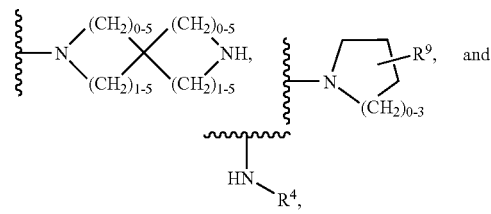

wherein
$R^4$ is chosen from

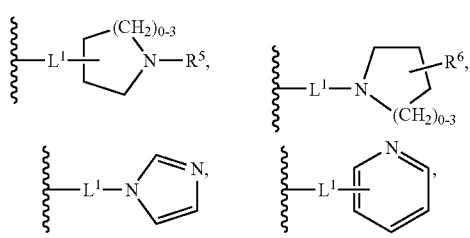

and —M—$NR^7R^8$;

wherein $R^5$, $R^6$, and $R^9$ are independently chosen from —H, $C_1$-$C_4$ alkyl, —OH, —OCH$_3$, halogen, and aminoalkyl;

$R^7$ and $R^8$ are independently chosen from —H, $C_1$-$C_4$ alkyl, and aminoalkyl;

$L^1$ is a bond or a $C_1$-$C_{10}$ alkylene optionally substituted with —OH, with a proviso that —OH cannot be bonded to a carbon atom that is also bonded to N;

M is $C_2$-$C_{10}$ alkyl optionally substituted with —OH, with a proviso that —OH cannot be bonded to a carbon atom that is also bonded to N;

$R^2$ is chosen from

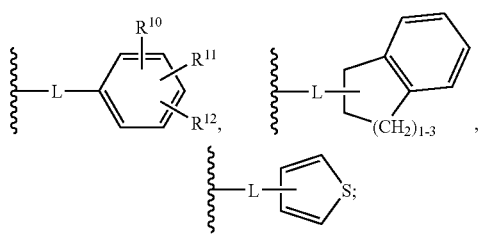

wherein $R^{10}$, $R^{11}$, and $R^{12}$ are independently chosen from —H, halogen, —OCH$_3$, —OCF$_3$, —CF$_3$, $C_1$-$C_4$ alkyl, and phenyl; and L is a bond or a $C_1$-$C_{10}$ alkylene.

11. A compound, or salt thereof, according to claim 10, wherein:

$R^4$ is chosen from

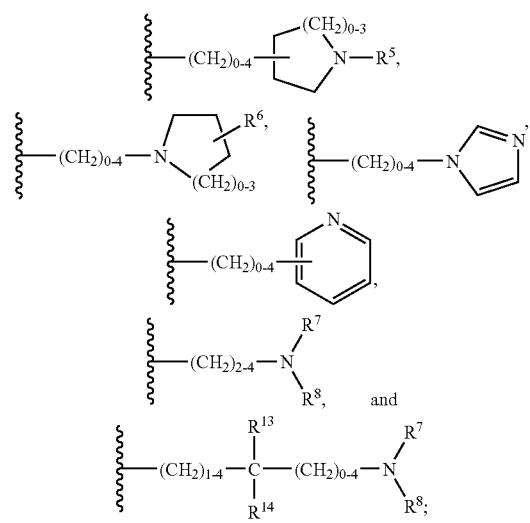

wherein $R^5$, $R^6$, and $R^9$ are independently chosen from —H, $C_1$-$C_4$ alkyl, —OH, —OCH$_3$, halogen, and aminoalkyl;

$R^7$ and $R^8$ are independently chosen from —H, $C_1$-$C_4$ alkyl, and aminoalkyl; and $R^{13}$ and $R^{14}$ are independently chosen from —H, —OH, and $C_1$-$C_4$ alkyl, with a proviso that —OH cannot be bonded to a carbon atom that is also bonded to N.

12. A compound, or salt thereof, according to claim 11, wherein:

$R^5$, $R^6$, $R^7$, and $R^8$ are independently chosen from —H and $C_1$-$C_4$ alkyl;

$R^9$ is —$R^{17}$—NR$^7$R$^8$; and wherein $R^{17}$ is a $C_1$-$C_4$ alkyl.

13. A compound, or salt thereof, according to claim 12, wherein:

$R^4$ is chosen from

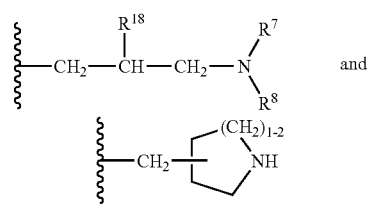

wherein $R^7$ and $R^8$ are independently chosen from —H and —CH$_3$; and $R^{18}$ is chosen from —H and —OH.

14. A compound, or salt thereof, according to claim 10, wherein:

$R^2$ is chosen from

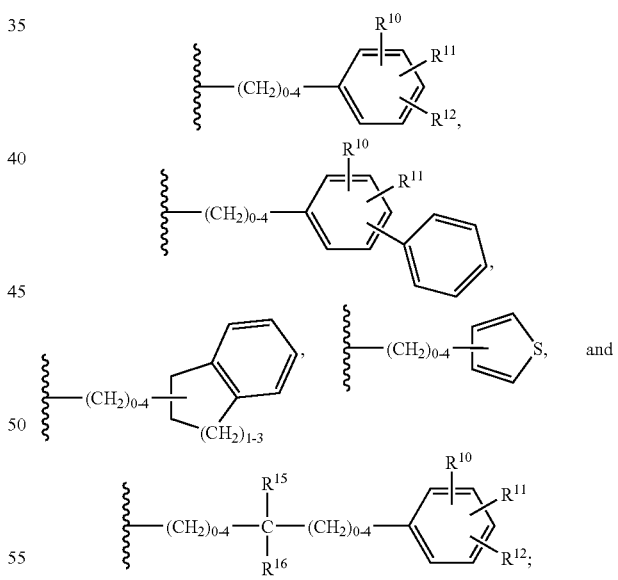

wherein $R^{10}$, $R^{11}$, and $R^{12}$ are independently chosen from —H, halogen, —OCH$_3$, —OCF$_3$, —CF$_3$, and $C_1$-$C_4$ alkyl; and $R^{15}$ and $R^{16}$ are independently chosen from —H and $C_1$-$C_4$ alkyl.

15. A pharmaceutical composition comprising a compound according to claim 10, or salt thereof, and a pharmaceutically acceptable carrier.

16. A compound, or salt thereof, represented by Formula I,

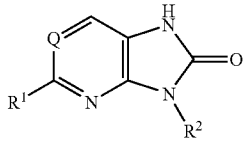

wherein:

Q is N;

$R^1$ is chosen from

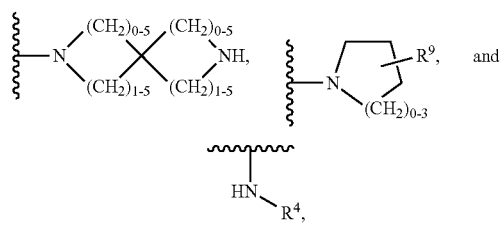

wherein $R^4$ is chosen from

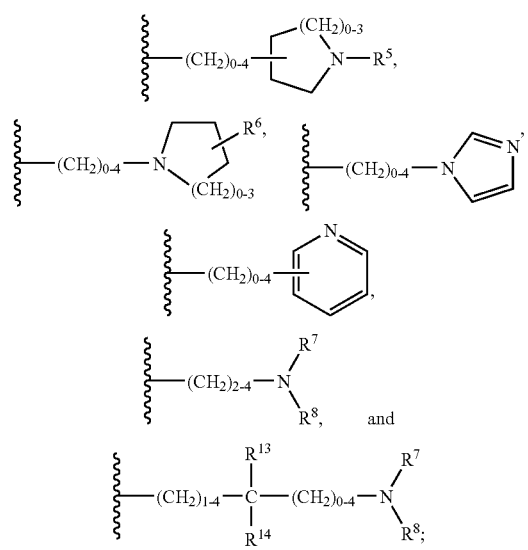

wherein $R^5$, $R^6$, and $R^9$ are independently chosen from —H, $C_1$-$C_4$ alkyl, —OH, —OCH$_3$, halogen, and aminoalkyl;

$R^7$ and $R^8$ are independently chosen from —H, $C_1$-$C_4$ alkyl, and aminoalkyl; and $R^{13}$ and $R^{14}$ are independently chosen from —H, —OH, and $C_1$-$C_4$ alkyl, with a proviso that —OH cannot be bonded to a carbon atom that is also bonded to N;

$R^2$ is chosen from

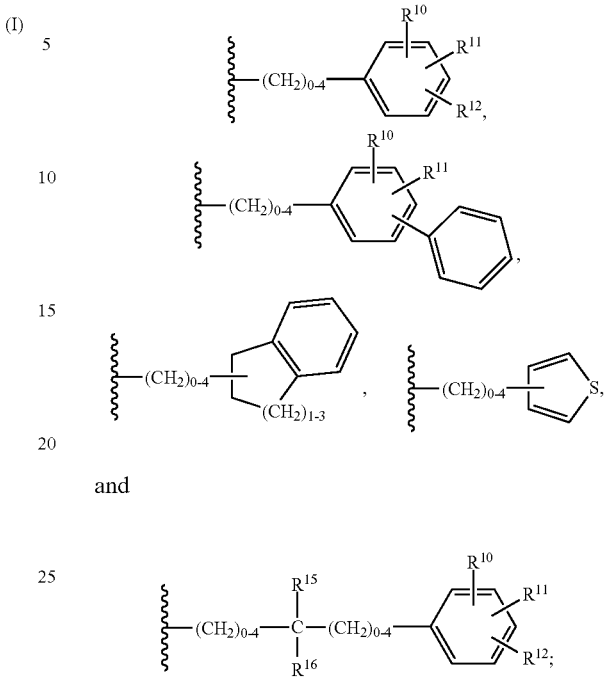

wherein $R^{10}$, $R^{11}$, and $R^{12}$ are independently chosen from —H, halogen, —OCH$_3$, —OCF$_3$, —CF$_3$, and $C_1$-$C_4$ alkyl; and $R^{15}$ and $R^{16}$ are independently chosen from —H and $C_1$-$C_4$ alkyl.

17. A compound, or salt thereof, according to claim 16, wherein:

$R^5$, $R^6$, $R^7$, and $R^8$ are independently chosen from —H and $C_1$-$C_4$ alkyl;

$R^9$ is —$R^{17}$—N$R^7R^8$; and wherein $R^{17}$ is a $C_1$-$C_4$ alkylene.

18. A compound, or salt thereof, according to claim 17, wherein:

$R^4$ is chosen from

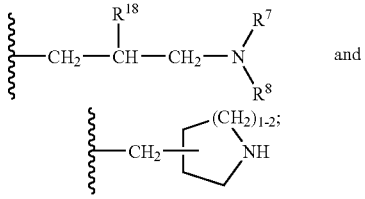

wherein $R^7$ and $R^8$ are independently chosen from —H and —CH$_3$; and $R^{18}$ is chosen from —H and —OH.

19. A pharmaceutical composition comprising a compound according to claim 16, or salt thereof, and a pharmaceutically acceptable carrier.

* * * * *

UNITED STATES PATENT AND TRADEMARK OFFICE
CERTIFICATE OF CORRECTION

PATENT NO.       : 7,989,459 B2
APPLICATION NO.  : 11/701632
DATED            : August 2, 2011
INVENTOR(S)      : Andrew Roughton et al.

It is certified that error appears in the above-identified patent and that said Letters Patent is hereby corrected as shown below:

Title Page, Column 2 (Abstract), Line 2, Change "PKCθ." to --PKCθ--.

Title Page, Column 2 (Abstract), Line 12, (Approx.), Change "hetroarylalkyl," to --heteroarylalkyl,--.

Title Page 2 (Item 56), Column 2, Line 19, Under Other Publications, change "hinhibitors" to --inhibitors--.

Title Page 2 (Item 56), Column 2, Line 42, Under Other Publications, change "Arthristis" to --Arthritis--.

At Column 2, Line 56, Change "hetroarylalkyl," to --heteroarylalkyl,--.

At Column 3, Line 43 (Approx.), Change "hetroarylalkyl," to --heteroarylalkyl,--.

At Column 4, Line 36-44 (Approx.),

Change " 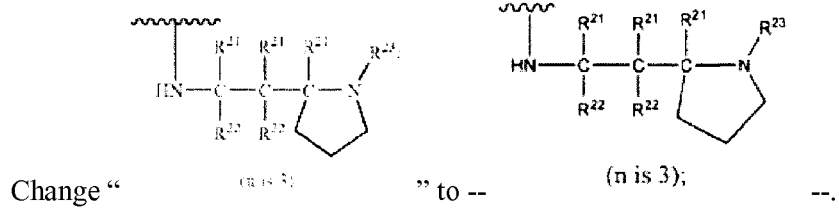 " to -- --.

Signed and Sealed this
Tenth Day of April, 2012

David J. Kappos
*Director of the United States Patent and Trademark Office*

At Column 6, Line 10-20 (Approx.),
wherein:

Change " 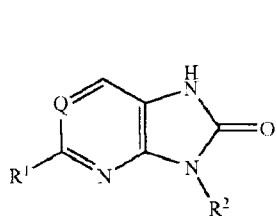 " to -- wherein: 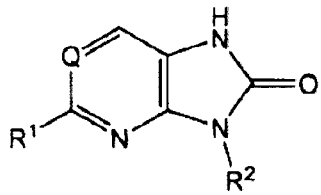 --.

At Column 8, Line 47-57 (Approx.)
wherein:

Change " 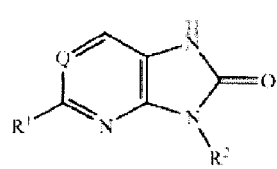 " to -- wherein: 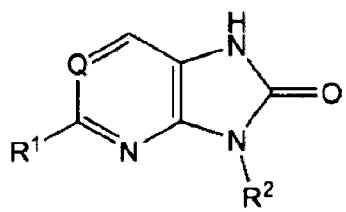 --.

At Column 12, Lines 19-20 (Approx.), Change "aminopenthyl," to --aminopentyl,--.

At Column 13, Line 10, Change "chromography" to --chromatography--.

At Column 14, Line 42 (Approx.), Change "trifloroacetic" to --trifluoroacetic--.

At Column 17, Line 32, Change "regiosiomer" to --regioisomer--.

At Column 21, Line 43 (Approx.), Change "Animation" to --Animation--.

At Column 35, Structure 207 Change " 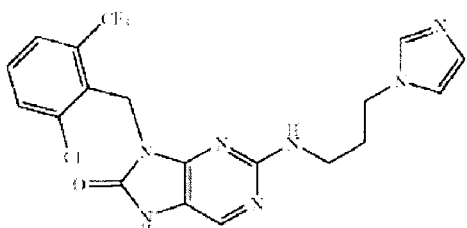 "

to -- 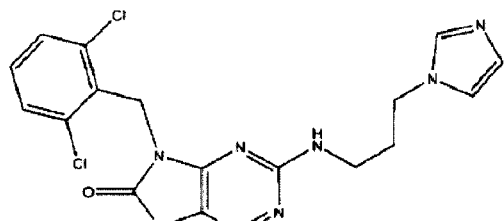 --.

CERTIFICATE OF CORRECTION (continued)
U.S. Pat. No. 7,989,459 B2

At Column 55, Lines 45-46 (Approx.), Change "immunosupression" to --immunosuppression--.

At Column 55, Line 48, Change "cyclosporin," to --cyclosporine,--.

At Column 58, Line 49, In Claim 1, change "di [($C_1$-$C_6$)alkyl]amino" to --di[($C_1$-$C_6$)alkyl]amino--.

At Column 58, Line 53, In Claim 1, change "hetroarylalkyl," to --heteroarylalkyl,--.

At Column 59, Line 53, In Claim 7, change "$R^{12}$," to --$R^{12}$--.